US012661614B2

(12) United States Patent
Meyer et al.

(10) Patent No.: US 12,661,614 B2
(45) Date of Patent: Jun. 23, 2026

(54) FILTER ASSEMBLY FOR A THERAPEUTIC GAS DELIVERY DEVICE

(71) Applicant: Mallinckrodt Pharmaceuticals Ireland Limited, Dublin (IE)

(72) Inventors: Andrew Meyer, Madison, WI (US); John Stanton, Madison, WI (US); Daniel Cody, Madison, WI (US)

(73) Assignee: Mallinckrodt Pharmaceuticals Ireland Limited, Dublin (IE)

( * ) Notice: Subject to any disclaimer, the term of this patent is extended or adjusted under 35 U.S.C. 154(b) by 326 days.

(21) Appl. No.: 18/441,201

(22) Filed: Feb. 14, 2024

(65) Prior Publication Data

US 2024/0269608 A1 Aug. 15, 2024

Related U.S. Application Data

(60) Provisional application No. 63/445,419, filed on Feb. 14, 2023.

(51) Int. Cl.
| | |
|---|---|
| *B01D 53/22* | (2006.01) |
| *A61M 16/08* | (2006.01) |
| *B01D 5/00* | (2006.01) |
| *B01D 63/06* | (2006.01) |
| *B01D 65/08* | (2006.01) |
| *B01D 71/36* | (2006.01) |

(52) U.S. Cl.
CPC ....... *B01D 53/226* (2013.01); *A61M 16/0808* (2013.01); *B01D 5/0072* (2013.01); *B01D 63/06* (2013.01); *B01D 65/08* (2013.01); *B01D 71/36* (2013.01); *B01D 2053/223* (2013.01); *B01D 2257/80* (2013.01)

(58) Field of Classification Search
CPC .... B01D 53/226; B01D 5/0072; B01D 63/06; B01D 65/08; B01D 71/36; B01D 2053/223; B01D 2053/22; B01D 2257/80; A61B 5/097; A61M 16/0808; A61M 2016/102; A61M 2205/7536; A61M 16/085
USPC .......... 95/43, 45, 52; 96/4, 7, 9; 128/203.12, 128/205.12, 205.27
See application file for complete search history.

(56) References Cited

U.S. PATENT DOCUMENTS

| | | | |
|---|---|---|---|
| 2,521,785 | A | 9/1950 | Minor et al. |
| 3,010,537 | A | 11/1961 | Ovid et al. |

(Continued)

FOREIGN PATENT DOCUMENTS

| | | |
|---|---|---|
| CA | 2089411 A1 | 8/1993 |
| CA | 2021750 C | 6/2000 |

(Continued)

OTHER PUBLICATIONS

International Search Report and Written Opinion for Application No. PCT/IB2024/051399, mailed on Jul. 1, 2024, 23 pages.

(Continued)

*Primary Examiner* — Frank M Lawrence, Jr.
(74) *Attorney, Agent, or Firm* — Polsinelli PC

(57) ABSTRACT

Disclosed herein is a sample gas filter assembly for a therapeutic gas delivery device. The sample gas filter assembly can have a filter apparatus, a water-permeable tubular membrane, and a ventilated cap. The sample gas filter assembly may be configured for maintaining a condensate pH from an assembly for humidity conditioning and filtering a sample gas in a therapeutic gas delivery device.

20 Claims, 10 Drawing Sheets

(56)                    References Cited

U.S. PATENT DOCUMENTS

| | | | |
|---|---|---|---|
| 3,458,050 A | 7/1969 | Cooper et al. | |
| 3,850,815 A * | 11/1974 | Furukawa | B01D 63/06 |
| | | | 210/321.89 |
| 3,910,998 A | 10/1975 | Vamashita et al. | |
| 4,028,444 A | 6/1977 | Brown et al. | |
| 4,138,591 A | 2/1979 | Baur et al. | |
| 4,273,938 A | 6/1981 | Merger et al. | |
| 4,297,588 A | 10/1981 | Hastbacka | |
| 4,366,131 A | 12/1982 | Fox | |
| 4,487,618 A | 12/1984 | Mann | |
| 4,558,708 A | 12/1985 | Labuda | |
| 4,613,369 A | 9/1986 | Koehler | |
| 4,690,759 A | 9/1987 | Mandy | |
| 4,825,863 A | 5/1989 | Dittmar et al. | |
| 4,865,815 A | 9/1989 | Martin et al. | |
| 4,874,408 A | 10/1989 | Overby | |
| 4,886,528 A | 12/1989 | Aaltonen | |
| 5,098,729 A | 3/1992 | Engel | |
| 5,186,166 A | 2/1993 | Riggs et al. | |
| 5,226,932 A * | 7/1993 | Prasad | B01D 53/226 |
| | | | 96/6 |
| 5,368,021 A | 11/1994 | Beard et al. | |
| 5,826,575 A | 10/1998 | Lall | |
| 5,926,575 A | 7/1999 | Ohzeki et al. | |
| 6,007,608 A | 12/1999 | Johnson | |
| 6,117,214 A | 9/2000 | Gerd et al. | |
| 6,210,469 B1 | 4/2001 | Tokar | |
| 6,305,913 B1 | 10/2001 | Hashish et al. | |
| 6,773,589 B2 | 8/2004 | Sharkey | |
| 7,879,062 B2 | 2/2011 | Galdonik et al. | |
| 2002/0116910 A1 | 8/2002 | Berger | |
| 2003/0064271 A1 | 4/2003 | Stenersen | |
| 2003/0131848 A1 | 7/2003 | Stenzler | |
| 2003/0167927 A1 | 9/2003 | Ostberg | |
| 2006/0042626 A1 | 3/2006 | Bunke et al. | |
| 2006/0130883 A1 | 6/2006 | Niedzwiecki et al. | |
| 2006/0139384 A1 | 6/2006 | Kitabatake et al. | |
| 2007/0204924 A1 | 9/2007 | Delgiacco et al. | |
| 2007/0246049 A1 | 10/2007 | Takeda et al. | |
| 2007/0277485 A1 | 12/2007 | Mackenzie et al. | |
| 2008/0066542 A1 | 3/2008 | Gao | |
| 2008/0114301 A1 | 5/2008 | Bandhauer et al. | |
| 2008/0114303 A1 | 5/2008 | Tremaglio | |
| 2009/0013873 A1 | 1/2009 | Larsen et al. | |
| 2009/0084383 A1 | 4/2009 | Maxeiner et al. | |
| 2009/0178970 A1 | 7/2009 | Stanfel et al. | |
| 2009/0223514 A1 | 9/2009 | Smith et al. | |
| 2009/0227939 A1 | 9/2009 | Mernoe et al. | |
| 2009/0301045 A1 | 12/2009 | Nelson et al. | |
| 2010/0012127 A1 | 1/2010 | Roth et al. | |
| 2010/0043787 A1 | 2/2010 | Fine et al. | |
| 2010/0134303 A1 | 6/2010 | Perkins | |
| 2010/0307341 A1 | 12/2010 | Peter et al. | |
| 2010/0313532 A1 | 12/2010 | Stjernfelt et al. | |
| 2011/0067699 A1 | 3/2011 | Caruso et al. | |
| 2011/0147299 A1 | 6/2011 | Stanfel et al. | |
| 2011/0283884 A1 | 11/2011 | Larsen et al. | |
| 2012/0017907 A1 | 1/2012 | Hsiao | |
| 2012/0097567 A1 | 4/2012 | Zhao et al. | |
| 2012/0136269 A1 | 5/2012 | Weckstrom | |
| 2012/0186328 A1 | 7/2012 | Makino et al. | |
| 2012/0211411 A1 | 8/2012 | Hopkins | |
| 2013/0345573 A1 | 12/2013 | Kargar et al. | |
| 2014/0044600 A1 | 2/2014 | McAlister | |
| 2014/0150794 A1 | 6/2014 | Kendrick et al. | |
| 2014/0157982 A1 * | 6/2014 | Ardanese | B01D 46/84 |
| | | | 95/20 |
| 2014/0246365 A1 | 9/2014 | McPeak et al. | |
| 2014/0250845 A1 | 9/2014 | Jackson et al. | |
| 2014/0275857 A1 | 9/2014 | Toth et al. | |
| 2014/0311963 A1 | 10/2014 | Bortnik et al. | |
| 2015/0031801 A1 | 1/2015 | Moon et al. | |
| 2015/0209528 A1 | 7/2015 | Lee et al. | |
| 2015/0223728 A1 * | 8/2015 | Fudge | A61M 16/021 |
| | | | 600/532 |
| 2015/0258479 A1 | 9/2015 | Gruber et al. | |
| 2015/0292455 A1 | 10/2015 | Metz et al. | |
| 2015/0352306 A1 | 12/2015 | Scheiner et al. | |
| 2016/0015885 A1 | 1/2016 | Pananen et al. | |
| 2016/0031733 A1 | 2/2016 | Scheurer | |
| 2016/0051747 A1 | 2/2016 | Wegener et al. | |
| 2016/0058968 A1 | 3/2016 | Yatsevich et al. | |
| 2016/0235273 A1 | 8/2016 | Buesing | |
| 2017/0144128 A1 | 5/2017 | Carrion et al. | |
| 2017/0281051 A1 | 10/2017 | Evans et al. | |
| 2017/0281896 A1 | 10/2017 | Biba et al. | |
| 2017/0319810 A1 | 11/2017 | Stanton et al. | |
| 2018/0250490 A1 | 9/2018 | Burgess et al. | |
| 2018/0296790 A1 | 10/2018 | Zapol et al. | |
| 2020/0001238 A1 | 1/2020 | Bahar et al. | |
| 2020/0360650 A1 * | 11/2020 | Cortez, Jr. | A61M 16/08 |
| 2021/0197120 A1 * | 7/2021 | Kani | H01M 8/04 |
| 2021/0213232 A1 | 7/2021 | Kendrick et al. | |
| 2022/0249795 A1 | 8/2022 | Tiwari | |
| 2024/0189498 A1 * | 6/2024 | Gruen | A61M 1/784 |

FOREIGN PATENT DOCUMENTS

| | | |
|---|---|---|
| CN | 101095637 A | 1/2008 |
| CN | 102369419 A | 3/2012 |
| CN | 102597721 A | 7/2012 |
| CN | 104374340 A | 2/2015 |
| CN | 104524916 A | 4/2015 |
| CN | 104707448 A | 6/2015 |
| CN | 109152906 B | 3/2021 |
| EP | 0370604 A1 | 5/1990 |
| EP | 0777111 A1 | 6/1997 |
| EP | 1695731 A1 | 8/2006 |
| EP | 1873501 A1 | 1/2008 |
| EP | 2878327 A1 | 6/2015 |
| EP | 4043084 A1 | 8/2022 |
| FR | 2655154 A1 | 5/1991 |
| JP | S60216226 A | 10/1985 |
| JP | H10318819 A | 12/1998 |
| JP | 2003305134 A | 10/2003 |
| JP | 2006159708 A | 6/2006 |
| JP | 2007020601 A | 2/2007 |
| JP | 2008006293 A | 1/2008 |
| JP | 2011172941 A | 9/2011 |
| JP | 2012163544 A | 8/2012 |
| KR | 960010375 B1 | 7/1996 |
| KR | 101313993 B1 | 10/2013 |
| WO | 0032295 A2 | 6/2000 |
| WO | 2006091594 A1 | 8/2006 |
| WO | 2011018669 A2 | 2/2011 |
| WO | 2015167347 A1 | 11/2015 |
| WO | 2016036260 A1 | 3/2016 |
| WO | 2020176481 A1 | 9/2020 |

OTHER PUBLICATIONS

Third Office Action for the Chinese Patent Application No. 201780025587.3, mailed on Aug. 25, 2021, 11 Pages.
American Heritage Dictionary of the English Language, Fifth Edition, 2016, Houghton Mifflin Harcourt Publishing Company, retrieved from the internet: URL: https://www. thefreedictionary. com/housing, 1 page.
Chen et al., "Critical Care Emergency Medicine", Second Military Medical University Press, Sep. 2007, p. 280.
Definition of Circumferential, Mar. 29, 2019,1 Page, Dictionary. com.
"Density" The American Heritage Dictionary of the English Language [online], Fourth Edition copyright by Houghton Mifflin Company, 2000, Retrieved from the Internet: URL: https://web. archive.org/web/20120201043247/https://www.thefreedictionary. com/density. 2009, 1 page.
Examination Report for European application No. 17714098.5 dated May 11, 2021, 4 pages.
Examination Report No. 1 for Australian Patent Application No. 2017260617 dated Jun. 2, 2021, 5 pages.
Examination Report No. 1 for Australian Patent Application No. 2022201286 dated Mar. 15, 2023, 4 pages.

(56) References Cited

OTHER PUBLICATIONS

Examination Report No. 2 for Australian Patent Application No. 2017260617 dated Mar. 17, 2022, 5 Pages.

Extended European Search Report for Application No. 21198359.8, dated Dec. 17, 2021, 9 pages.

Extended European Search Report for Application No. 22159290.0, dated Jun. 24, 2022, 6 pages.

Extended European Search Report for European Application No. 17776200.2, mailed Nov. 12, 2019, 7 pages.

Extended European Search Report for European Application No. 23205363.7, mailed on Jan. 26, 2024, 9 pages.

First Office Action and Search Report for Chinese Patent Application No. 202110183182.0, dated Nov. 22, 2023, 18 pages.

Ichinose F., et al., "Inhaled Nitric Oxide, A Selective Pulmonary Vasodilator: Current Uses and Therapeutic Potential," Circulation, Jun. 29, 2004, vol. 109, pp. 3106-3111.

International Preliminary Report on Patentability for International Application No. PCT/US2017/020100, mailed Oct. 11, 2018, 8 pages.

International Preliminary Report on Patentability for International PCT Patent Application No. PCT/US2017/022403, mailed on Nov. 15, 2018, 10 pages.

International Preliminary Report on Patentability for International PCT Patent Application No. PCT/US2017/022643, mailed on Nov. 15, 2018, 10 pages.

International Search Report and Written Opinion for International Application No. PCT/US2017/020100, mailed May 19, 2017, 9 pages.

International Search Report and Written Opinion for International Application No. PCT/US2017/022403, dated Jun. 8, 2017, 14 Pages.

International Search Report and Written Opinion for International Application No. PCT/US2017/022643, mailed May 29, 2017, 13 pages.

Liu J., "Complete Collection of Practical Technologiesfor Design, Construction and Maintenance of Pipeline Engineering," ChinaBuilding Materials Industry Press, Aug. 31, 1999, pp. 2452-2455.

"Mount," American Heritage Dictionary of the English Language, Houghton Mifflin Harcourt Publishing Company, Fifth Edition, 2016, 1 page, Retrieved from the Internet: URL: https://www.thefreedictionary.com/mounted.

Non Final Office Action for U.S. Appl. No. 18/223,909, mailed on Feb. 12, 2024, 8 pages.

Non-Final Office Action for U.S. Appl. No. 17/666,983, mailed on Aug. 17, 2023, 20 pages.

Notice of Allowance and Fee(s) due for U.S. Appl. No. 16/724,786 mailed on Sep. 15, 2022, 11 pages.

Notice of Preliminary Rejection for Korean Application No. 10-2018-7026796 mailed on Jan. 24, 2022, 7 pages.

Notice of Preliminary Rejection for Korean Application No. 10-2022-7012756 mailed on Jan. 26, 2023, 6 pages.

Notice of Preliminary Rejection for Korean Application No. 10-2022-7012756 mailed on Jul. 13, 2022, 18 pages.

Notice of Preliminary Rejection for Korean Application No. 10-2022-7012756 mailed on Jul. 25, 2023, 6 pages.

Office Action for Australian Application No. 2022206805, mailed on Jul. 27, 2023, 3 pages.

Office Action for Canadian Application No. 3,017,337 mailed on Jan. 20, 2023, 6 pages.

Office Action for Canadian Application No. 3,022,664 mailed on May 29, 2023, 3 pages.

Office Action for Chinese Patent Application No. 201780018853.X, mailed Feb. 10, 2022, 16 Pages.

Office Action for Japanese Application No. 2021-013045, mailed on Oct. 7, 2022, 6 pages.

Office Action for Japanese Patent Application No. 2018553203, mailed Mar. 15, 2017, 7 pages.

Office Action for Japanese Patent Application No. 2021013045, mailed Dec. 27, 2021, 7 pages.

Office Action for Korean Application No. 10-2022-7032976, mailed on Dec. 22, 2023, 14 pages.

Office Action for Korean Application No. 10-2022-7032976, mailed on May 30, 2023, 10 pages.

Office Action for Korean Patent Application No. 10-2018-7029443, mailed on Mar. 25, 2022, 9 pages.

Office Action for Korean Patent Application No. 10-2018-7034472, mailed on Jun. 28, 2021, 19 pages.

Office Action for Korean Patent Application No. 20187029443, mailed Jun. 16, 2021, 22 pages.

Office action for Mexican Application No. MX/a/2018/013220 dated Sep. 8, 2021, 7 pages.

Office Action for New Zealand Application No. 747898, mailed on Aug. 25, 2023, 4 pages.

Office Action for New Zealand Application No. 747898, mailed on Mar. 14, 2024, 5 pages.

Office Action for U.S. Appl. No. 17/666,983, mailed on Apr. 17, 2023, 23 pages.

Office Action for U.S. Appl. No. 17/666,983, mailed on Oct. 31, 2022, 12 pages.

Office Action for U.S. Appl. No. 18/082,174, mailed on Apr. 24, 2023, 16 pages.

Perry R.H., et al., "Membrane Separation Processes," Chemical Engineers handbook, The McGraw-Hill Companies Inc, 1999, pp. 22-37.

Second Office Action for Chinese Application No. 201780018853. X, mailed Apr. 15, 2021, 16 pages.

Third Office Action for Chinese Application No. 201780018853.X, mailed Sep. 14, 2021, 15 pages.

Final Office Action for U.S. Appl. No. 18/223,909 mailed on May 15, 2024, 11 Pages.

Second Office Action and Search Report for Chinese Patent Application No. 202110183182.0, dated Apr. 20, 2024, 14 pages.

International Search Report and the Written Opinion for PCT Application No. PCT/IB2024/051401, mailed on May 15, 2024, 15 pages.

* cited by examiner

700

Passing sample gas through a filter apparatus of an assembly ———— 702

Collecting a condensate from the sample gas in the filter apparatus ———— 704

Passing the filtered sample gas through a water-permeable tubular membrane ———— 706

800

Passing sample gas through a filter apparatus of an assembly — 802

Collecting a condensate from the sample gas in the filter apparatus — 804

Passing the filtered sample gas through a water-permeable tubular membrane — 806

900

| | |
|---|---|
| Passing sample gas through a filter apparatus of an assembly | — 902 |
| Collecting a condensate from the sample gas in the filter apparatus | — 904 |
| Passing the filtered sample gas through a water-permeable tubular membrane | — 906 |
| Preventing the sample gas from contacting a sensor without first being humidity conditioned at a confidence level of at least 98% | — 908 |

1000

FILTER ASSEMBLY FOR A THERAPEUTIC GAS DELIVERY DEVICE

CLAIM OF PRIORITY

This application claims the benefit of U.S. Provisional Application No. 63/445,419, filed on Feb. 14, 2023, the entire contents of which are herein incorporated by reference in its entirety.

FIELD

The present disclosure is directed to a patient sample gas filter assembly and methods of use thereof. More specifically, the present disclosure is directed to a patient sample gas filter assembly that includes a filtration system to filter liquids from sample gas in a therapeutic gas delivery system.

BACKGROUND

Therapeutic gas can be delivered to patients through inspiratory breathing gas flowing from a breathing circuit affiliated with a ventilator. For example, the therapeutic gas can be injected into inspiratory breathing gas flowing in the breathing circuit and, subsequently, delivered to the airways of the patient. One such therapeutic gas is nitric oxide, which can produce vasodilatory effects on a patient.

While administering therapeutic gas, a gas sensor module can monitor a portion of the inspiratory breathing gas to confirm that the therapeutic gas is being delivered at a desired dose in the inspiratory breathing gas flow. For example, a patient gas sample line and sample gas filter assembly can be used to provide sample gas (e.g., a portion of the inspiratory breathing gas flow) to a gas sensor module, which monitors the concentrations of the therapeutic gas being delivered to the patient. In some cases, the breathing circuit, which delivers the therapeutic gas to the airways of the patient, can be humidified. Traditionally, the patient gas sample line and sample gas filter assembly involved a complex design to separate the liquid from the sample gas. However, these designs can be difficult to manufacture and can require the patient gas sample line and sample gas filter assembly to be in a specific orientation during use. Moreover, these designs can allow wicking between various stages of filtration, which can cause premature occlusion. Traditionally, water-permeable tubing has been used to filter moisture out of the sample gas before the sample gas enters into a filter. However, water-permeable tubing can react with saline in the sample gas to produce hydrochloric acid which corrodes sampling sensors and other components, causing the need for replacement components well before the desired lifetime. Additionally, the saline in the sample gas can react with the water-permeable tubing causing occlusion within the water-permeable tubing.

Therefore, there is a need for a patient gas sample line and sample gas filter assembly that is more convenient to manufacture, is more convenient to use, and is long-lasting.

SUMMARY

Aspects of the present disclosure include an assembly for a therapeutic gas delivery device. The assembly can include a filter apparatus, a water-permeable tubular membrane, and a ventilated cap. The filter apparatus can have an inlet, an outlet, at least one reservoir, and at least one filter membrane. The filter membrane may be located between the inlet and the outlet. The filter apparatus may be operable to remove water vapor from the sample gas and collect a condensate in the at least one reservoir. The water-permeable tubular membrane may be fluidly connected to the outlet of the filter apparatus. The ventilated cap may be connected to the filter apparatus and surround the outlet. The ventilated cap may have a ventilation aperture.

In certain instances, the water-permeable tubular membrane can be configured to humidity condition the sample gas.

In certain instances, the ventilated cap can have a plurality of ventilation apertures. In certain instances, the ventilated cap is configured to contain and secure the water-permeable tubular membrane.

In certain instances, the water-permeable tubular membrane is formed of a sulfonated tetrafluoroethylene based fluoropolymer-copolymer. In certain instances, the water-permeable tubular membrane is tubing comprising a sulfonated tetrafluoroethylene based fluoropolymer-copolymer.

Aspects of the present disclosure include a filter apparatus for a therapeutic gas delivery device. The filter apparatus can have a housing, a first chamber, and a second chamber. The housing can include a sample gas inlet and sample gas outlet. The sample gas inlet can be operable to receive a gas sample from a sample line connected to an inspiratory line of the therapeutic gas delivery device. The first chamber can be located in the housing and have a first filter membrane and a first reservoir located between the sample gas inlet and the first filter membrane. The second chamber can be located in the housing and have a second filter membrane and a second reservoir located between the first filter membrane and the sample gas outlet.

In certain instances, the first reservoir and second reservoir are oriented axially such that the filter apparatus can be operable to be used in any axial orientation. In certain instances, the housing, each of the chambers, and each of the filter membranes can have a substantially circular cross-section.

In certain instances, the at least one reservoir can be large enough to accommodate water for 12 hours of continuous use. In certain instances, the at least on reservoir can have a volume of at least 10 cubic centimeters. In certain instances, the assembly can be configured to be installed in the therapeutic gas delivery device with one hand.

Aspects of the present disclosure include a method for humidity conditioning and filtering a sample gas in a therapeutic gas delivery device. The method can include passing sample gas through a filter apparatus of an assembly, collecting a condensate from the sample gas in the filter apparatus, and passing the filtered gas through a water-permeable tubular membrane of the assembly. The sample gas leaving the water-permeable tubular membrane can be a humidity conditioned sample gas.

In certain instances, the sample gas leaving the water-permeable tubular membrane can be a humidity conditioned sample gas at a confidence level of at least 98%.

In certain instances, the outer surfaces of the water-permeable tubular membrane can be exposed to an ambient air flow.

In certain instances, the humidity conditioned sample gas can be substantially free of saline. In certain instances, production of hydrochloric acid (HCl) can be reduced or prevented within the therapeutic gas delivery device.

In certain instances, a blockage of a sample line connected to the assembly, a blockage of a pump connected to the sample line, corrosion of the filter apparatus, and/or corrosion in the therapeutic gas device can be reduced or prevented at a confidence level of at least 98%.

In certain instances, the assembly can maintain the condensate at a pH of about 5.0 to about 6.0.

Aspects of the present disclosure include a method for preventing degradation or corrosion in a therapeutic gas delivery device. The method can include passing the sample gas through a filter apparatus of an assembly, collecting a condensate from the sample gas in the filter apparatus, passing the filtered sample gas through a water-permeable tubular membrane of the assembly, and preventing the sample gas from contacting a sensor without first being humidity conditioned at a confidence level of at least 98% and/or maintaining the condensate at a pH of about 5.0 to about 6.0 at a confidence level or at least 98%. The sample gas leaving the water-permeable tubular membrane can be a humidity conditioned sample gas.

BRIEF DESCRIPTION OF THE DRAWINGS

The description will be more fully understood with reference to the following figures and data graphs, which are presented as various embodiments of the disclosure and should not be construed as a complete recitation of the scope of the disclosure. It is noted that, for purposes of illustrative clarity, certain elements in various drawings may not be drawn to scale. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Figure 1:
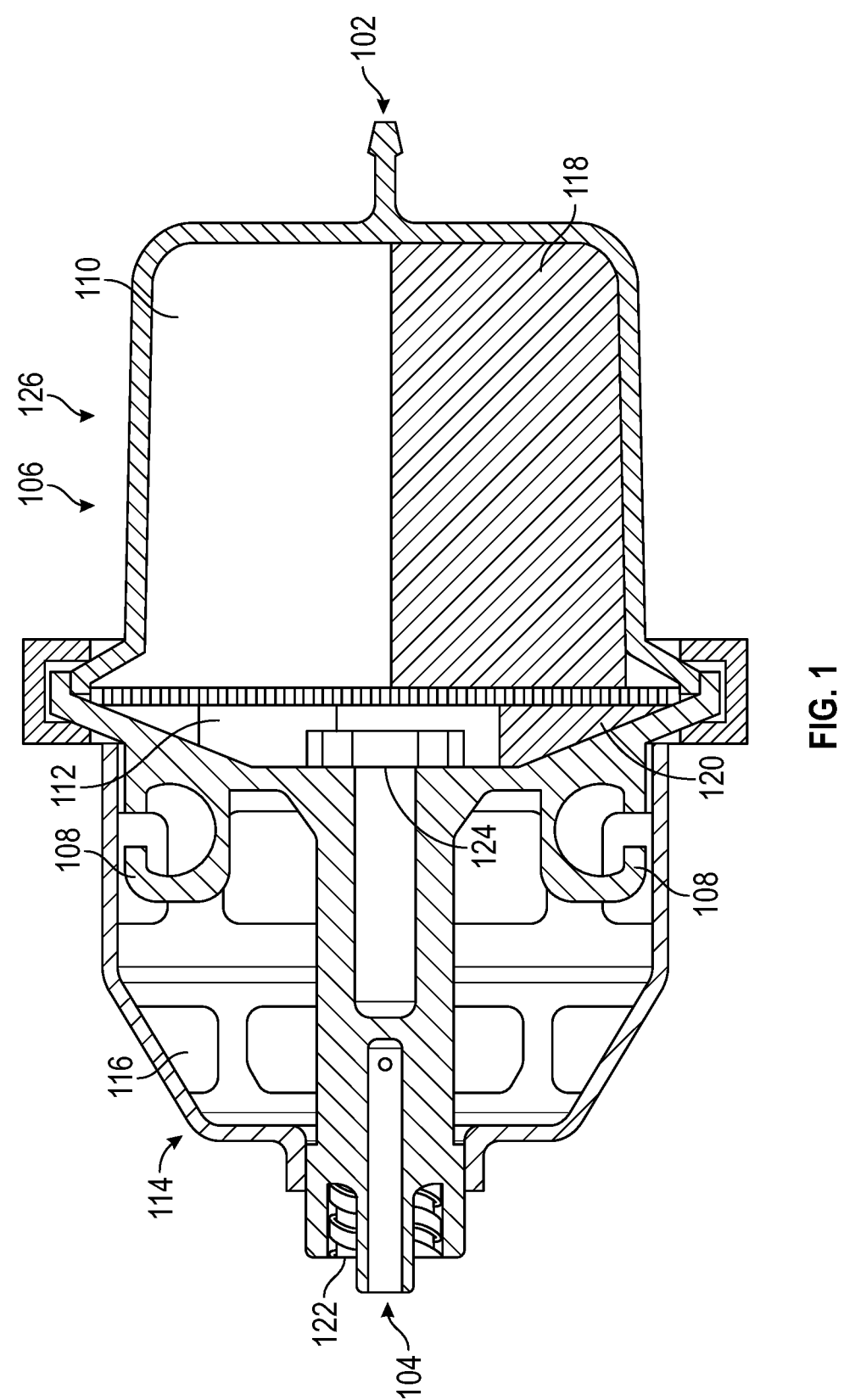
FIG. 1 is a cross-sectional view of a sample gas filter assembly.

It will be appreciated that for simplicity and clarity of illustration, where appropriate, reference numerals have been repeated among the different figures to indicate corresponding or analogous elements. In addition, numerous specific details are set forth in order to provide a thorough understanding of the examples described herein. However, it will be understood by those of ordinary skill in the art that the examples described herein can be practiced without these specific details. In other instances, methods, procedures and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

Several definitions that apply throughout the above disclosure will now be presented.

The term "coupled" as used herein is defined as connected, whether directly or indirectly through intervening components, and is not necessarily limited to physical connections. The connection can be such that the objects are permanently connected or releasably connected.

The term "substantially" is defined to be essentially conforming to the particular dimension, shape or other word that substantially modifies, such that the component need not be exact.

The terms "comprising," "including" and "having" are used interchangeably in this disclosure. The terms "comprising," "including" and "having" mean to include, but not necessarily be limited to the things so described.

The terms "filter" and "filtration" are used herein in their broadest sense to encompass any and all of various types and degrees of removal or separation of liquid from gas, and may also include removal of other non-liquid particulates if present in some cases.

The term "liquid" is used herein in its broadest sense to encompass humidity, water vapor, moisture from humidified air, other liquids in a vapor state, nebulized liquids, nebulized medical solutions (e.g., saline solution) and suspensions, etc.

The terms "humidity condition" and "humidity conditioning" refer to adjusting the relative humidity of a gas (e.g. the sample gas) to match the humidity of the ambient air. Therefore, either humidity will flow into the sample gas when the sample gas has a relative humidity lower than the ambient air or humidity will flow out of the sample gas when the sample gas has a relative humidity greater than the ambient air.

The present disclosure relates to a patient gas sample line and sample gas filter assembly and methods of use thereof. The filter includes a multi-stage filtration system with a liquid reservoir, which filters liquid from sample gas (e.g., a portion of a mixture of the breathing gas and therapeutic gas) containing the liquid. The liquid component may be any removable liquid, such as, for example, humidity, water vapor, moisture from humidified air, other liquids in a vapor state, nebulized liquids, nebulized medical solutions (e.g., saline solution) and suspensions, etc.

The sample gas filter assembly can be used with a therapeutic gas delivery system that delivers a therapeutic gas (e.g., nitric oxide) to the airways of a patient. The therapeutic gas is delivered to the patient by dosing into the breathing circuit, usually in line with a mechanical ventilator. A subsystem of the therapeutic gas delivery system contains a gas sensor module with one or more gas sensors, which monitor the concentrations of the therapeutic gas and/or other gasses delivered to the patient. The gas sensor module is connected to the same patient breathing circuit as the therapeutic gas delivery system.

The sample gas filter assembly can be more convenient to use than a traditional patient gas sample line and filter. For example, the sample gas filter assembly can be easier to manufacture (e.g., it may involve only one or two manufacturing steps). Additionally, the sample gas filter assembly can be used in any axial orientation.

Traditionally, sample gas filter assemblies are configured to receive sample gas from a patient breathing circuit at a gas sample tee. The sample gas is then transferred to a filter through a water-permeable tubular membrane. However, this configuration of the sample gas filter assembly, a water-permeable tubular membrane delivering sample gas to a filter, results in issues with corrosion and occlusion along the flow path and into the gas sensor module. When the sample gas enters the water-permeable tubular membrane before being filtered, the water-permeable tubular membrane can react with cations found in the sample gas, such as sodium found in saline. The water-permeable tubular membrane can contain sulfonic acid receptor sites in a polytetrafluoroethylene (PTFE) matrix. These sites can bind with any cation, (e.g., sodium, found in saline, which is commonly used in therapeutic gases). When the sodium in the sample gas binds to the water-permeable tubular membrane, chlorine is left free to bind to hydrogen, creating hydrochloric acid. When hydrochloric acid is created in vapor form, it will not be captured by the filter apparatus and can flow into the gas sensor module, thereby corroding sample sensors, sample pumps, and other components within the therapeutic gas delivery device. Corrosion caused by hydrochloric acid can also occur in the filter apparatus. Additionally, when the sodium cations of the saline react with the water-permeable tubular membrane a build-up can occur, creating occlusion in the water-permeable tubular membrane.

The present disclosure discloses a novel solution to the problems of the interactions of saline with a water-permeable tubular membrane. By reconfiguring the sample gas filter assembly to filter the sample gas through a filter apparatus prior to allowing the sample gas to flow through the water-permeable tubular membrane, the sodium chloride can be filtered prior to coming in contact with the water-permeable tubular membrane. By filtering the sodium chloride before it contacts the water-permeable tubular membrane, the issues of downstream corrosion and occlusion are avoided.

FIG. 1 illustrates one instance of a sample gas filter assembly 100. The sample gas filter assembly 100 can include a sample gas inlet 102, a sample gas outlet 124, an assembly outlet 104, a filter apparatus 106 (e.g., sample gas filter), a ventilated cap 114, and a water-permeable tubular membrane (not shown in FIG. 1).

The filter apparatus 106 can include a housing 126 that has a sample gas inlet 102 and a sample gas outlet 124. The sample gas inlet 102 can be in fluid communication with the sample gas outlet 124, thereby establishing a fluid flow path through the filter apparatus 106 (e.g., from the sample gas inlet 102 to the sample gas outlet 124).

The sample gas inlet 102 can receive sample gas into the filter apparatus 106. In one example, the sample gas inlet 102 can receive sample gas from a first portion of a sample line (e.g., via a gas sample tee) that is connected to an inspiratory line of a therapeutic gas delivery device. For example, the sample gas inlet 102 can be removably coupled to a sample line, which can be removably coupled to the inspiratory line at a sample gas tee, thereby establishing fluid communication between the inspiratory line and the filter apparatus 106. In another example, the sample gas line can be connected to an expiratory line of the therapeutic gas delivery system. In other examples, the sample gas line can be connected to any kind of gas line where sampling a gas or combination of gases to determine concentrations is desired.

The sample gas outlet 124 can discharge sample gas from the filter apparatus 106. The sample gas can then flow through a water-permeable tubular membrane, as discussed below. The sample gas can flow out of the sample gas filter assembly 100 at the assembly outlet 104 where it can be delivered by a second portion of the sample line to a gas sensor module in a therapeutic delivery device. The assembly outlet 104 can be configured to removably couple to a fitting (e.g., luer fitting). For example, in one instance, the assembly outlet 104 can extend outwards (e.g., away) from the sample gas filter assembly 100 and can include external threads 122 to removably couple to a fitting. In another instance, the assembly outlet 104 can include internal threads to removably couple to a fitting. The configuration (e.g., external or internal threads) of the assembly outlet 104 can be the opposite gender of a connector (e.g., at the sample gas inlet 102) of the first portion of the sample line, so that the sample gas filter assembly is unidirectional.

A sample gas pump can be used to pump sample gas through the sample gas filter assembly 100 to the gas sensor module. The sample gas pump can produce fluid flow of the sample gas from the sample gas inlet 102 through the assembly outlet 104 and into the gas sensor module.

A first chamber 110 can be located within the housing 126. In other words, the housing 126 of the filter apparatus 106 can define, in whole or in part, the first chamber 110. In one instance, the first chamber 110 can have a substantially circular cross-section, which can define a diameter of the first chamber 110. The first chamber 110 can contain a first reservoir 118. The filter apparatus 106 can remove liquids (e.g., humidity, water vapor, moisture from humidified air, other liquids in a vapor state, nebulized liquids, nebulized medical solutions and suspensions, etc.) from the sample gas (e.g., via a filter membrane, discussed in further detail below) and collect the liquids in the first reservoir 118. The first reservoir 118 can be oriented axially along the length of the filter so that the filter apparatus 106 can operate (e.g., remove liquids from the sample gas and collect the liquids) in any orientation during operation. The first reservoir 118 can define a volume and, in some instances, can be configured to accommodate liquid for approximately twelve hours of continuous use before it needs to be replaced and/or emptied.

The volume of the first reservoir 118 can be about 5 cubic centimeters to about 10 cubic centimeters, about 10 cubic centimeters to about 15 cubic centimeters, about 15 cubic centimeters to about 20 cubic centimeters, about 20 cubic centimeters to about 25 cubic centimeters, about 25 cubic centimeters to about 30 cubic centimeters, about 30 cubic centimeters to about 35 cubic centimeters, about 35 cubic centimeters to about 40 cubic centimeters, about 40 cubic centimeters or more.

A second chamber 112 can be located within the housing 126. In other words, the housing 126 of the filter apparatus 106 can define, in whole or in part, the second chamber 112. In one instance, the second chamber 112 can have a substantially circular cross-section, which can define a diameter of the second chamber 112. The second chamber 112 can contain a second reservoir 120. The filter apparatus 106 can remove liquids (e.g., humidity, water vapor, moisture from humidified air, other liquids in a vapor state, nebulized liquids, nebulized medical solutions and suspensions, etc.) from the sample gas (e.g., via a filter membrane, discussed in further detail below) and collect the liquids in the second reservoir 120. The second reservoir 120 can be oriented axially along the length of the filter so that the filter apparatus 106 can operate (e.g., remove liquids from the sample gas and collect the liquids) in any orientation during operation. The second reservoir 120 can define a volume and, in some instances, can be configured to accommodate liquids for approximately twelve hours of continuous use before it needs to be replaced.

The second reservoir 120 can have a volume of about 1 cubic centimeter to about 5 cubic centimeters, about 5 cubic centimeters to about 10 cubic centimeters, about 10 cubic centimeters to about 15 cubic centimeters, about 15 cubic centimeters to about 20 cubic centimeters, about 20 cubic centimeters or more. In some examples, the second reservoir 120 can have a volume less than the volume first reservoir 118. In another example, the second reservoir 120 can have a volume greater than a volume of the first reservoir 118. In some examples, the first reservoir 118 and the second reservoir 120 can have the same or substantially the same volume.

The sample gas filter assembly 100 can include a ventilated cap 114. The ventilated cap can comprise one or more ventilation apertures 116. The ventilation apertures can be rectangular in shape, as shown in FIG. 1. The ventilation apertures 116 may have other shapes, as illustrated, for example, in FIGS. 3-6. The ventilation apertures 116 can have any shape such that air can flow into the ventilated cap 114. The ventilated cap 114 can be configured to contain and secure a water-permeable tubular membrane. For example, the ventilated cap 114 can have water-permeable tubular membrane holders 108 to secure a water-permeable tubular membrane.

Figure 2:
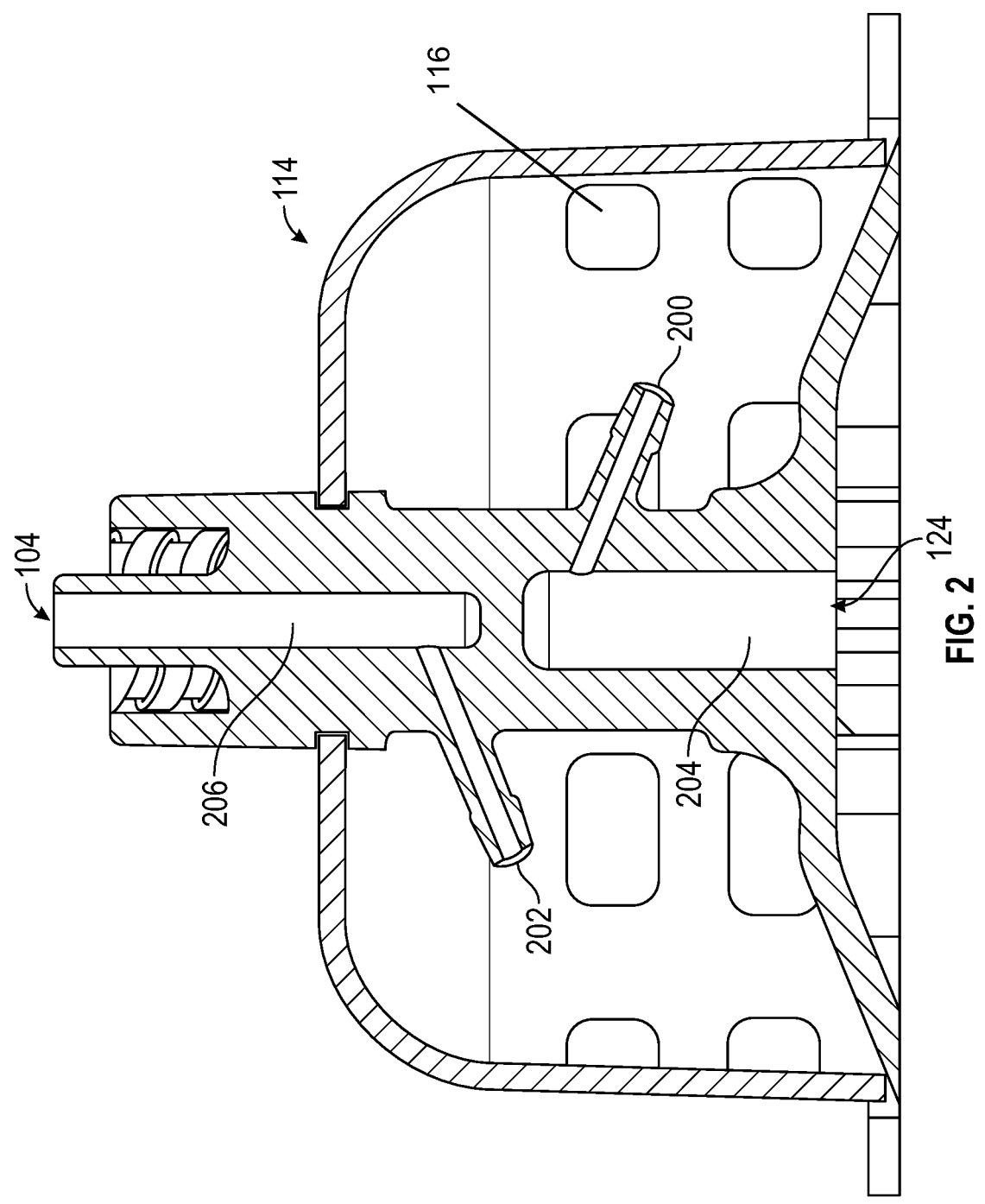
FIG. 2 is a cross-sectional view of a ventilated cap.

FIG. 2 illustrates one instance of a ventilated cap 114. The sample gas filter assembly 100 can have a ventilated cap 114 comprising a plurality of ventilation apertures 116. The gas filter assembly 100 can include a water-permeable tubular membrane inlet conduit 204, a water-permeable tubular membrane inlet port 200, a water-permeable tubular membrane outlet port 202, a sample gas outlet conduit 206, a sample gas outlet 124, and an assembly outlet 104.

A water-permeable tubular membrane (not shown in FIG. 2) can be connected to the water-permeable tubular membrane inlet port 200 and the water-permeable tubular membrane outlet port 202, thereby establishing a fluid flow path between the water-permeable tubular membrane inlet port 200 and the water-permeable tubular membrane outlet port 202. The water-permeable tubular membrane inlet conduit 204 can supply sample gas to the water-permeable tubular membrane at the water-permeable tubular membrane inlet port 200. The sample gas outlet conduit 206 can allow sample gas to flow from the water-permeable tubular membrane outlet port 202 to the assembly outlet 104.

In one instance, the water-permeable tubular membrane inlet port 200 may connect to the water-permeable tubular membrane inlet conduit 204 at a 30-degree angle, as illustrated, for example, in FIG. 2. Sample gas may be provided to the water-permeable tubular membrane by flowing out of the sample gas outlet 124, through the water-permeable tubular membrane inlet conduit 204, and into the water-permeable tubular membrane at the water-permeable tubular membrane inlet port 200.

The water-permeable tubular membrane inlet port 200 may connect to the water-permeable tubular membrane inlet conduit 204 at about a 10-degree angle to about a 20-degree angle, about a 20-degree angle to about a 30-degree angle, about a 30-degree angle to about a 40-degree angle, about a 40-degree angle to about a 50-degree angle, about a 50-degree angle to about a 60-degree angle, about a 60-degree angle to about a 70-degree angle, about a 70-degree angle to about a 80-degree angle, about a 80-degree angle to about a 90-degree angle (as illustrated, for example, in FIG. 3), about a 90-degree angle to about a 100-degree angle, about a 100 degree angle to about a 110-degree angle, about a 110-degree angle to about a 120-degree angle, about a 120-degree angle to about a 130-degree angle, about a 130-degree angle to about a 140-degree angle, about a 140-degree angle to about a 150-degree angle, about a 150-degree angle to about a 160-degree angle, or about a 160-degree angle to about a 170-degree angle.

The water-permeable tubular membrane outlet port 202 may be connected to the sample gas outlet conduit 206 at a 30-degree angle, as illustrated, for example, in FIG. 2. Sample gas can exit the water-permeable tubular membrane at the water-permeable tubular membrane outlet port 202 and flow through the sample gas outlet conduit 206 to the assembly outlet 104.

The water-permeable tubular membrane outlet port 202 may be connected to the outlet conduit at a 10-degree angle to about a 20-degree angle, about a 20-degree angle to about a 30-degree angle, about a 30-degree angle to about a 40-degree angle, about a 40-degree angle to about a 50-degree angle, about a 50-degree angle to about a 60-degree angle, about a 60-degree angle to about a 70-degree angle, about a 70-degree angle to about a 80-degree angle, about a 80-degree angle to about a 90-degree angle (as illustrated, for example, in FIG. 3), about a 90-degree angle to about a 100-degree angle, about a 100-degree angle to about a 110-degree angle, about 1 110-degree angle to about a 120-degree angle, about a 120-degree angle to about a 130-degree angle, about a 130-degree angle to about a 140-degree angle, about a 140-degree angle to about a 150-degree angle, about a 150-degree angle to about a 160-degree angle, or about a 160-degree angle to about a 170-degree angle.

Figure 3:
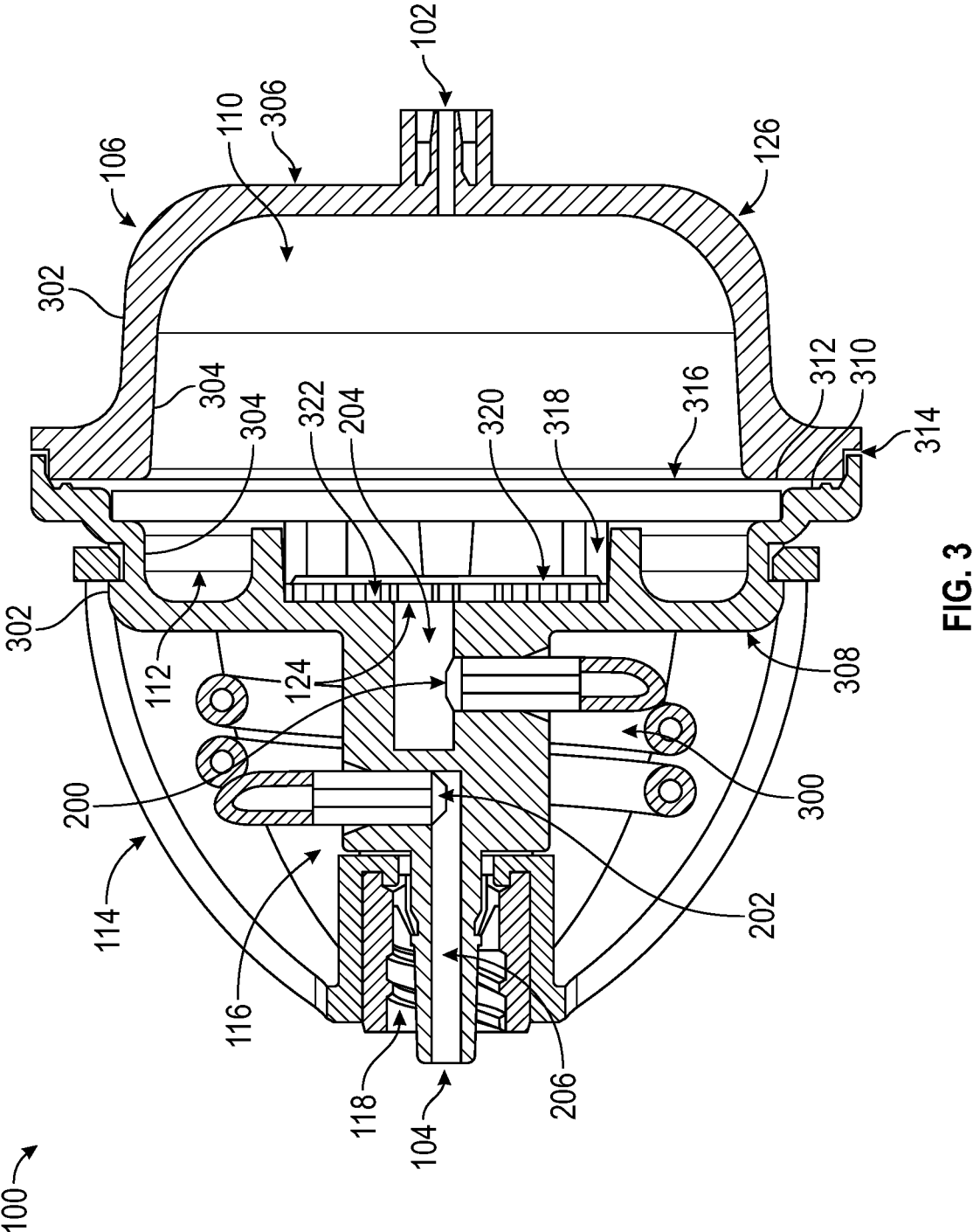
FIG. 3 is a cross-sectional view of a sample gas filter assembly.

FIG. 3 illustrates an instance of a sample gas filter assembly 100. The sample gas filter assembly 100 can include a filter apparatus 106 that has a sample gas inlet 102 and a sample gas outlet 124. The sample gas filter assembly 100 can have a ventilated cap 114 configured to surround and contain a water-permeable tubular membrane 300 and having a sample gas outlet 124 and an assembly outlet 104. The sample gas inlet 102 can be in fluid communication with the assembly outlet 104, thereby establishing a fluid flow path through the sample gas filter assembly 100 (e.g., from the sample gas inlet 102 to the assembly outlet 104).

The housing 126 of the filter apparatus 106 can define an exterior surface 302 and an interior surface 304 opposite the exterior surface 302, as illustrated, for example in FIG. 3. The housing 126 thickness can be defined by the distance between the exterior surface 302 and the interior surface 304. The housing can have a substantially circular cross-section, which can define a diameter of the housing 126.

In one instance, the housing 126 can include a first shell 306 and a second shell 308, which can each define a portion of the exterior surface 302 and the interior surface 304 of the housing 126. The first shell 306 can define a first surface 312 opposite the sample gas inlet 102. The second shell 308 can define a second surface 310 opposite the sample gas outlet 124. The first surface 312 of the first shell 306 can, in whole or in part, abut the second surface 310 of the second shell 308 to form a housing 126 that is watertight. In one instance, an ultrasonic weld 314 can couple the first shell 306 and the second shell 308 at the first surface 312 and the second surface 310.

A first chamber 110 can be located within the housing 126. In other words, the housing 126 of the filter apparatus 106 can define, in whole or in part, the first chamber 110. In one instance, the first chamber 110 is partially defined by the interior surface 304 of the first shell 306. In one instance, the first chamber 110 can have a substantially circular cross-section, which can define a diameter of the first chamber 110.

A second chamber 112 can be located within the housing 126. In other words, the housing 126 of the filter apparatus 106 can define, in whole or in part, the second chamber 112. In one instance, the second chamber 112 is partially defined by the interior surface 304 of the second shell 308. In one instance, the second chamber 112 can have a substantially circular cross-section, which can define a diameter of the second chamber 112.

A first filter membrane 316 (e.g., first stage of filtration), as illustrated, for example, in FIG. 3 can be included in the first chamber 110. In one instance, the first filter membrane 316 can be substantially circular in shape, which can define a diameter of the first filter membrane 316. The first filter membrane 316 can remove liquids (e.g., humidity, water vapor, moisture from humidified air, other liquids in a vapor state, nebulized liquids, nebulized medical solutions and suspensions, etc.) from the sample gas (e.g., sample gas flowing through the first filter membrane 316) and can cause liquid to coalesce and collect in a first reservoir 118 (e.g., front reservoir), as illustrated, for example, in FIG. 1. In some instances, the first filter membrane 316 can be coalescing to liquid being both oleophobic and hydrophobic. In one instance, the first filter membrane 316 can be a glass fiber filter membrane.

Figure 6:
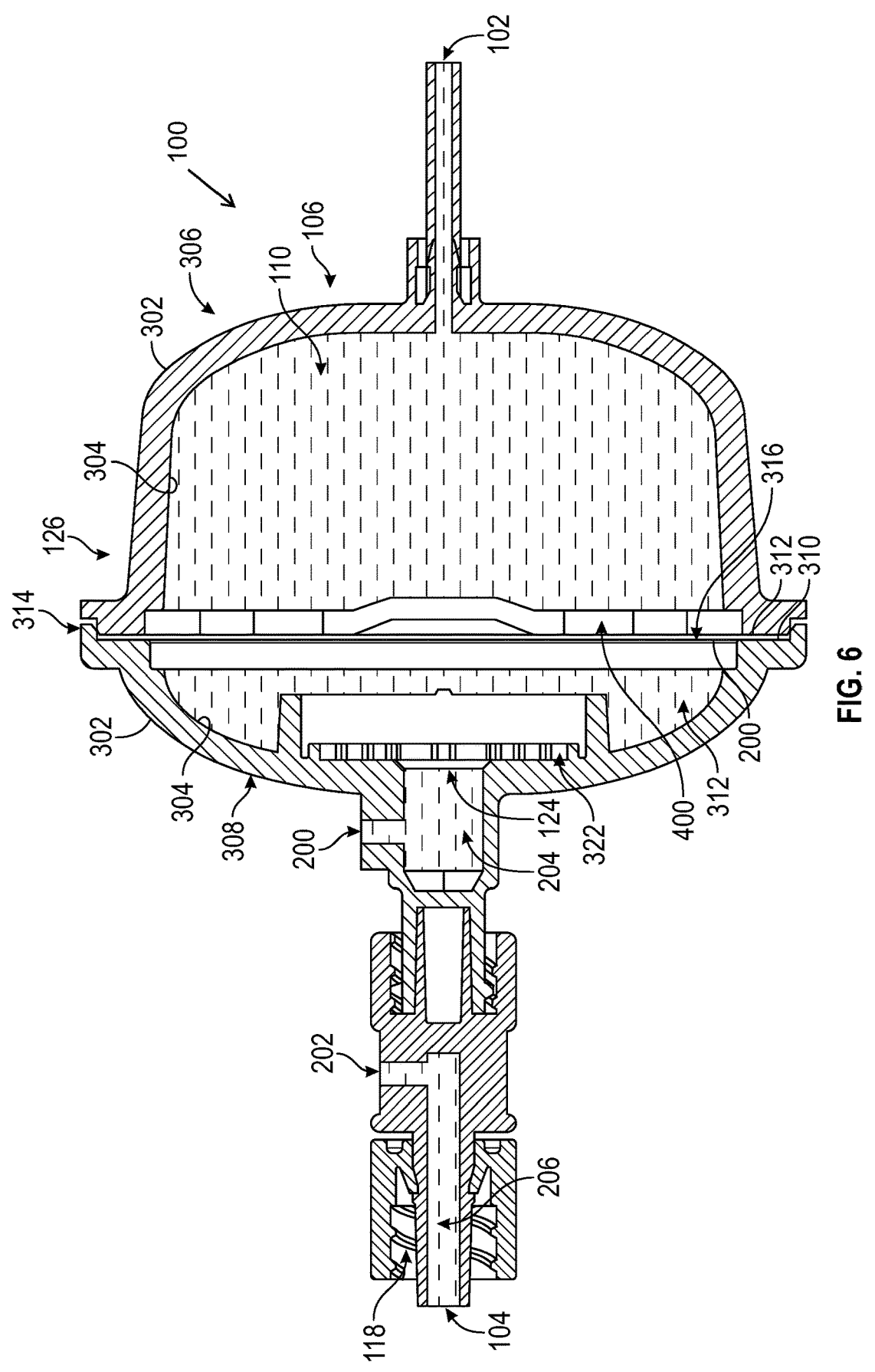
FIG. 6 is a cross-sectional view of a sample gas filter assembly.

In some instances, the first filter membrane 316 can be held in position (e.g., secured) and/or sealed by the abutment of the first surface 312 of the first shell 306 and the second surface 310 of the second shell 308, as illustrated, for example, in FIGS. 3 and 6. For example, an ultrasonic weld 314 that couples the first surface 312 and the second surface 310 can secure and/or seal the first filter membrane 316.

A first reservoir 118, as illustrated, for example, in FIG. 1, can be included in the first chamber 110 (e.g., integrated into the housing 126). In some instances, the first reservoir 118 can be located between the sample gas inlet 102 and the first filter membrane 316. In other instances, the first reservoir can be located between the sample gas inlet 102 and a baffle plate (discussed in further detail below). The filter apparatus 106 can remove liquids (e.g., humidity, water vapor, moisture from humidified air, other liquids in a vapor state, nebulized liquids, nebulized medical solutions and suspensions, etc.) from the sample gas (e.g., via the first filter membrane 316) and collect the liquids in the first reservoir 118. The first reservoir can be oriented axially along the length of the filter so that the filter apparatus 106 can operate (e.g., remove liquids from the sample gas and collect the liquids) in any orientation during operation. The first reservoir 118 can define a volume and, in some instances, can be configured to accommodate water for approximately twelve hours of continuous use before it needs to be replaced.

A second filter membrane 320 (e.g., second stage of filtration), as illustrated, for example, in FIG. 3, can be included in the second chamber 112. In one instance, the second filter membrane can be substantially circular in shape, which can define a diameter of the second filter membrane 320. The second filter membrane 320 can remove liquids from the sample gas (e.g., sample gas flowing through the second filter membrane 320) and cause liquid to coalesce and collect in a second reservoir 120 (e.g., rear reservoir), as illustrated, for example, in FIG. 1. In some instances, the second filter membrane 320 can be a hydrophobic membrane.

The diameter of the second filter membrane 320 can, in some examples, be smaller than the diameter of the first filter membrane 316. In other words, the diameter of the first filter membrane 316 can be larger than the diameter of the second filter membrane 320, as illustrated, for example, in FIG. 3. The first filter membrane 316 and the second filter membrane 320 can, in some instances, be separated to prevent wicking between the first filter membrane 316 and the second filter membrane 320. For example, a gap may exist between the first filter membrane 316 and the second filter membrane 320 to prevent wicking, as illustrated, for example, in FIG. 3.

A second reservoir 120, as illustrated, for example, in FIG. 1, can be included in the second chamber 112 (e.g., integrated into the housing 126). In some instances, the second reservoir 120 can be located between the first filter membrane 316 and the sample gas outlet 124. In other instances, the second reservoir 120 can be located between a fiber membrane of the first chamber 110 and a press-fit baffle 318. The filter apparatus 106 can remove liquids (e.g., humidity, water vapor, moisture from humidified air, other liquids in a vapor state, nebulized liquids, nebulized medical solutions and suspensions, etc.) from the sample gas (e.g., via the second filter membrane 320) and collect liquids in the second reservoir 120. The second reservoir 120 can be oriented axially along the length of the filter so that the filter apparatus 106 can operate (e.g., remove liquids from the sample gas and collect the liquids) in any orientation during operation. The second reservoir 120 can define a volume and, in some instances, can be configured to accommodate water for approximately twelve hours of continuous use before it needs to be replaced.

The first reservoir 118 and the second reservoir 120 can be oriented axially so that the filter apparatus 106 can operate in any axial orientation. In some instances, the first reservoir 118 and the second reservoir 120 can be large enough (e.g., have enough volume) to accommodate water for at least twelve hours of continuous use. The volume of the second reservoir 120 can, in some instances, be smaller than the volume of the first reservoir 118. In other words, the volume of the first reservoir 118 can be larger than the volume of the second reservoir 120, as illustrated, for example, in FIG. 1.

A press-fit baffle 318 can be included in the second chamber 112, as illustrated, for example, in FIG. 3. In some examples, the press-fit baffle 318 can mechanically support the second filter membrane 320 on the first side (e.g., front side, which faces the flow of the sample gas) of the second filter membrane 320.

A labyrinth support 322, as illustrated, for example, in FIG. 3, can be included in the second chamber 112. The labyrinth support 322 can be located on the interior surface 304 of the housing 126 near the water-permeable tubular membrane inlet conduit 204 (e.g., the interior surface 304 of the second shell 308). In some examples, the labyrinth support 322 can mechanically support the second filter membrane 320 on the second side (e.g., backside, facing away from the flow of the sample gas) of the second filter membrane 320. Additionally, the labyrinth support 322 can promote effective circulation of the sample gas behind the second filter membrane 320.

The first filter membrane 316 and the second filter membrane 320 can both be hydrophobic and/or oleophobic. The hydrophobic and/or oleophobic elements of the first filter membrane 316 and the second filter membrane 320 can filter liquids (e.g., humidity, water vapor, moisture from humidified air, other liquids in a vapor state, nebulized liquids, nebulized medical solutions and suspensions, etc.) from the sample gas. One of the liquids that can be filtered is saline solution (e.g., NaCl). By filtering the sample gas before it enters the water-permeable tubular membrane 300, reactions between the sodium in saline solution and the water-permeable tubular membrane 300 are prevented or reduced. Preventing or reducing reactions between sodium, and other cations, and the water-permeable tubular membrane can eliminate the production of hydrochloric acid, therefore preventing corrosion caused by hydrochloric acid in the sample line, gas sensor module, filter apparatus, and therapeutic gas delivery device. Additionally, occlusion (e.g., blockage) of the sample line and water-permeable tubular membrane can be prevented or reduced by filtering the sample gas before it flows through the water-permeable tubular membrane.

The filter apparatus 106 can maintain a pH level of about 5.0 to about 6.0 in the condensate collected within the filter apparatus 106. By maintaining a pH level of about 5.0 to about 6.0, the filter apparatus 106 can ensure liquids that react with the water-permeable tubular membrane 300 (e.g., saline solution (NaCl)) within a sample gas are filtered before entering the water-permeable tubular membrane 300. Preventing NaCl from entering the water-permeable tubular membrane 300 prevents reactions between the water-permeable tubular membrane 300 and the sodium in saline therefore eliminating the risk of downstream corrosion or occlusion in the therapeutic gas delivery device and the sample gas filter assembly 100.

In other instances, the condensate can have a pH level of about 5.3 to about 6.0. In another instance, the condensate can have a pH level of about 5.4 to about 5.6.

The filtered sample gas, prior to entering the water-permeable tubular membrane 300, can be substantially free of saline. In some examples, the filtered sample gas can be about 98% to about 98.5%, about 98.5% to about 99%, about 99% to about 99.5%, about 99.5% to about 99.95%, about 99.95% to about 99.99% free of saline. In an example, the filtered sample gas can be substantially free of saline. In another example, the filter sample gas can be 100% free of saline.

The sample gas filter assembly 100 can include a ventilated cap 114 that can be connected to the filter apparatus 106. The ventilated cap 114 can be removably coupled to the second shell 308 of the filter apparatus 106 at the exterior surface 302. The ventilated cap can be removably coupled to the exterior surface 302 of the second shell 308 via a snap fit connection, as illustrated, for example, in FIG. 3. The ventilated cap can also be connected to the filter apparatus 106 using other connection methods such as screws, barb fit connections, or other connection mechanisms.

A water-permeable tubular membrane 300 can be fluidly connected to a water-permeable tubular membrane inlet port 200 on one end and a water-permeable tubular membrane outlet port 202 on another end, as illustrated, for example, in FIG. 3. The water-permeable tubular membrane 300 can be contained within the ventilated cap 114. The water-permeable tubular membrane 300 can be attached to water-permeable tubular membrane holders 108 to secure the water-permeable tubular membrane 300 within the ventilated cap. The water-permeable tubular membrane holders 108 may be in the shape of a hook as illustrated, for example, in FIG. 1.

In one example, the sample gas outlet 124 can discharge sample gas from the filter apparatus 106 to a water-permeable tubular membrane inlet conduit 204. The water-permeable tubular membrane inlet conduit 204 can provide filtered sample gas to a water-permeable tubular membrane 300 at the water-permeable tubular membrane inlet port 200. The water-permeable tubular membrane 300 can discharge sample gas at a water-permeable tubular membrane outlet port 202. Sample gas can flow through a sample gas outlet conduit 206 and be discharged to a gas sensor module of a therapeutic gas delivery device at the assembly outlet 104.

The water-permeable tubular membrane 300 can be formed of a sulfonated tetrafluoroethylene based fluoropolymer-copolymer. In one instance, the water-permeable tubular membrane 300 can be tubing made of a sulfonated tetrafluoroethylene based fluoropolymer-copolymer (e.g. Nafion®).

The water-permeable tubular membrane 300 can be configured to humidity condition the sample gas. The water-permeable tubular membrane 300 can be exposed to ambient air flow through the ventilation apertures 116 in the ventilated cap 114. The water-permeable tubular membrane 300 can humidity condition the sample gas by conditioning the sample gas to match the humidity of the ambient air. The water-permeable tubular membrane 300 can remove water vapor from the sample gas to reduce the sample gas' humidity to match the humidity of ambient air. In other examples, the water-permeable tubular membrane 300 can raise the humidity of the sample gas if the humidity of the sample gas is lower than the humidity of ambient air. The humidity conditioned sample gas can then flow through the assembly outlet 104 and into a gas sensor module where the sample gas can be analyzed. Humidity conditioning the sample gas before the sample gas enters the sensors of the gas sensor module provides for more accurate readings and promotes longevity of the sensors and other components in the therapeutic delivery device and sample gas filter assembly 100.

The humidity conditioned gas can be substantially free of saline. In some instances, the humidity conditioned gas can be 98%, 98.5%, 99%, 99.5%, 99.95%, or 99.99% free of saline.

Figure 4:
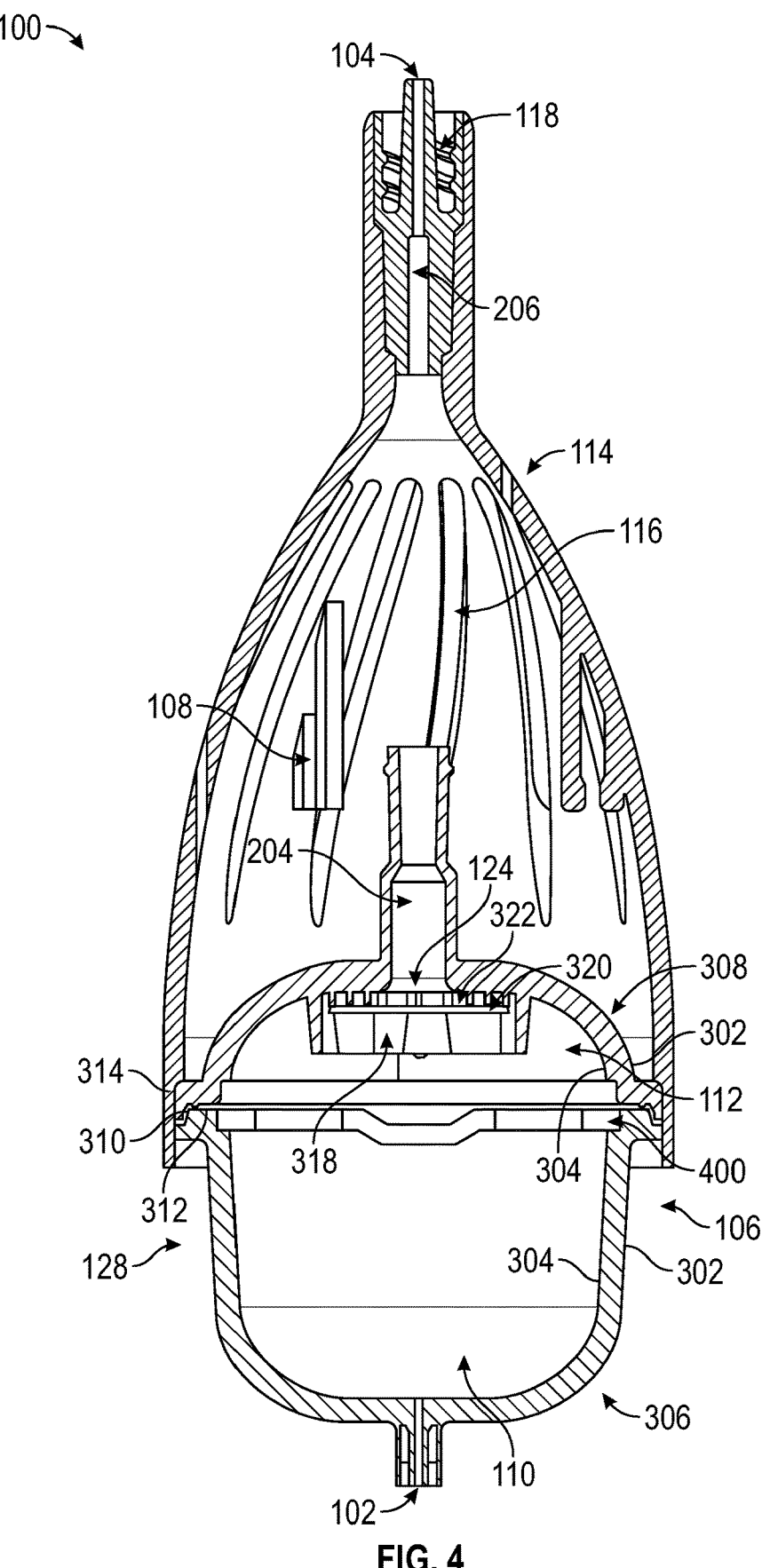
FIG. 4 is a cross-sectional view of a sample gas filter assembly.

FIG. 4. illustrates one instance of a sample gas filter assembly 100. A baffle plate 400 can, in some instances, be included in the first chamber 110, as illustrated, for example, in FIG. 4. In some examples, the baffle plate 400 can mechanically support the first filter membrane 316 on the second side (e.g., backside, facing away from the flow of the sample gas) of the first filter membrane 316.

Figure 5:
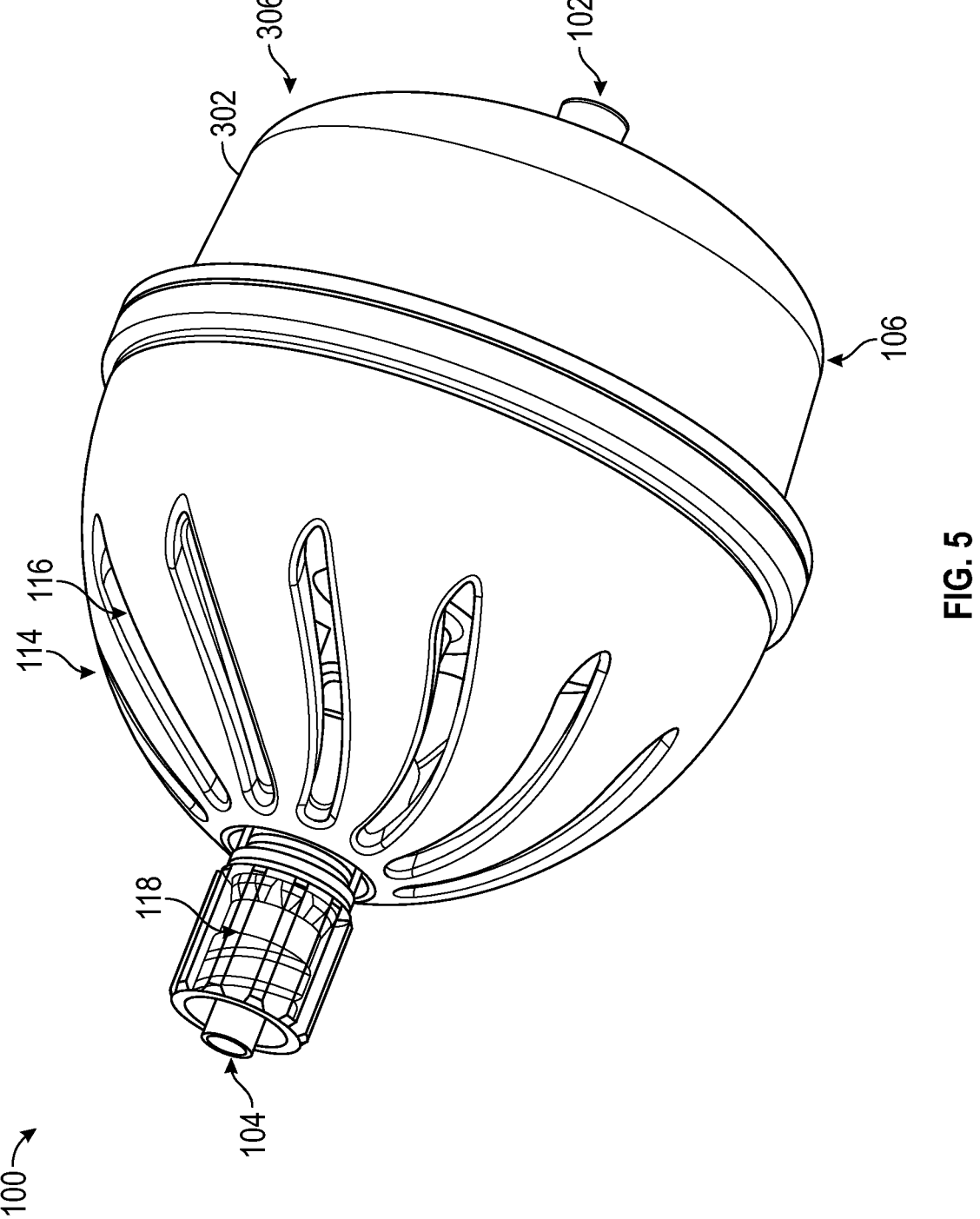
FIG. 5 is a perspective view of a sample gas filter assembly.

FIG. 5 illustrates one instance of a sample gas filter assembly 100. The sample gas filter assembly can provide a fluid flow path for sample gas from the sample gas inlet 102 to the assembly outlet 104. The sample gas filter assembly 100 can be configured to be installed with one hand.

FIG. 6 illustrates one instance of a sample gas filter assembly 100. A fiber membrane 600 can, in some instances, be included in the first chamber 110. In some examples, the fiber membrane 600 can mechanically support the first filter membrane 316 on the second side (e.g., backside, facing away from the flow of the sample gas) of the first filter membrane 316. In one instance, the fiber membrane 600 can be a course Vyon fiber membrane.

The sample gas filter assembly, including the sample line (the line which attaches to the sample gas inlet 102) and/or the sample gas filter assembly 100, can be removed and replaced as needed. In other words, an existing sample line and/or sample gas filter assembly 100 can be removed from the therapeutic gas delivery device and a new sample line and/or sample gas filter assembly 100 can be connected in its place, as previously described.

Figure 7:
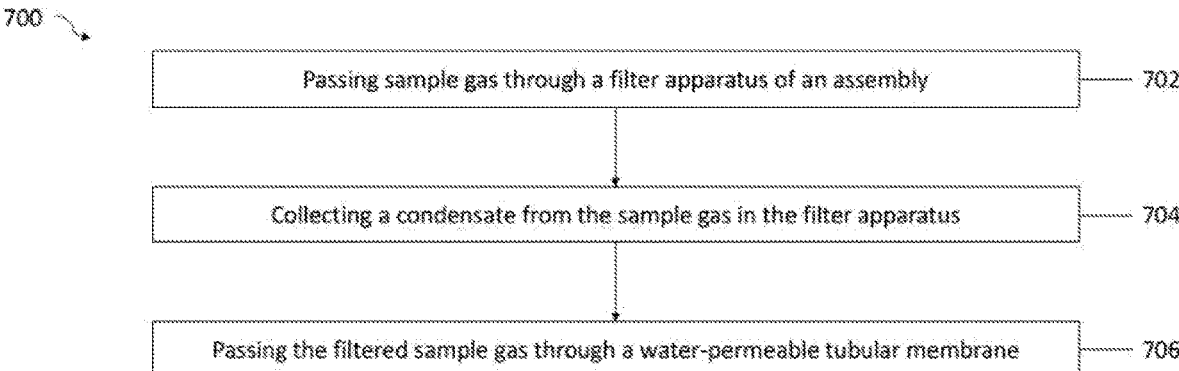
FIG. 7 is a flowchart of an example method.

Further provided herein is a method for humidity conditioning and filtering a sample gas in a therapeutic gas delivery device. A flowchart as seen in FIG. 7 is presented in accordance with an example embodiment. The method is provided by way of example, as there are a variety of ways to carry out the method. The method 700 described below can be carried out using the configurations illustrated in the figures, for example, and various elements of those figures are referenced in explaining example method 700. Each block represents one or more processes, methods, or subroutines, carried out in the example method 700. Furthermore, the illustrated order of blocks of FIG. 7 is illustrative only and the order of the blocks can change according to the present disclosure. Additional blocks may be added or fewer blocks may be utilized, without departing from this disclosure.

The example method 700 is a method for humidity conditioning and filtering a sample gas in a therapeutic gas delivery device. The example method can begin at block 702. At block 702, the method includes passing the sample gas through a filter apparatus (e.g., sample gas filter) of an assembly. The sample gas can be provided to the sample gas filter at a sample gas inlet. The sample gas can flow through the sample gas inlet to a first filter membrane. The first filter membrane may be hydrophobic and/or oleophobic. At the first filter membrane liquids (humidity, water vapor, moisture from humidified air, other liquids in a vapor state, nebulized liquids, nebulized medical solutions and suspensions, etc.) may be filtered out of the sample gas. The first filter membrane can also filter saline solution from the sample gas. The sample gas may then pass through a second filter membrane. At the second filter membrane, liquids (humidity, water vapor, moisture from humidified air, other liquids in a vapor state, nebulized liquids, nebulized medical solutions and suspensions, etc.) may further be filtered out of the sample gas.

At block 704, the method includes collecting a condensate from the sample gas in the filter apparatus. The liquids blocked by the first filter membrane can be collected in a first reservoir located in a first chamber of the sample gas filter. The first reservoir can also collect any saline solution blocked by the first filter membrane. The liquids may be collected in a second reservoir located in a second chamber of the sample gas filter. A condensate pH level of 5.0 to 6.0 may be maintained in the condensate collected. Maintaining the condensate at a pH level of 5.0 to 6.0 ensures that any salt, or sodium is filtered out before entering the water-permeable tubular membrane, preventing any reactions in the water-permeable tubular membrane that may produce hydrochloric acid.

At block 706, the method includes passing the filtered sample gas through a water-permeable tubular membrane of the assembly. The sample gas leaving the water-permeable tubular membrane is a humidity conditioned gas. The water-permeable tubular membrane can be contained in a ventilated cap connected to the sample gas filter. The ventilated cap can have at least one ventilation aperture to allow ambient air to contact the water-permeable tubular membrane. When the ambient air contacts the outer surfaces of the water-permeable tubular membrane, the water-permeable tubular membrane can release water vapor from the sample gas to humidity condition the sample gas. The sample gas is humidity conditioned to have the same humidity as the ambient air by the water-permeable tubular membrane.

The sample gas can be humidity conditioned at a confidence level of at least 98% to about 99%, about 99% to about 99.5%, about 99.5% to about 99.9%, about 99.9% to about 99.95%, or more. The humidity conditioned gas can be substantially free of saline. The humidity conditioned gas can be about 98% to about 99%, about 99% to about 99.5%, about 99.5% to about 99.95% free of saline. In some examples, the humidity conditioned gas can be substantially free of saline. In an example, the humidity conditioned gas can be 100% free of saline.

By filtering the liquids, including saline solution, before allowing the liquids to reach the water-permeable tubular membrane, the production of hydrochloric acid is prevented or reduced. Preventing or reducing the production of hydrochloric acid can greatly reduce corrosion of the filter apparatus and corrosion of the therapeutic gas delivery device. Additionally, by preventing sodium from reacting with the water-permeable tubular membrane, blockage of the sample line, sample pump, and/or water-permeable tubular membrane can be greatly reduced. A blockage of the sample line connected to the assembly, a blockage of a pump connected to the sample line, corrosion of the sample gas filter, and/or corrosion in the therapeutic gas delivery device can be reduced or prevented at a confidence level of 98%.

The assembly can maintain the condensate at a pH of about 5.0 to about 6.0. In another example, the assembly can maintain the condensate at a pH of about 5.3 to about 6.0. In a further example, the assembly can maintain the condensate at a pH of about 5.4 to about 5.6.

Figure 8:
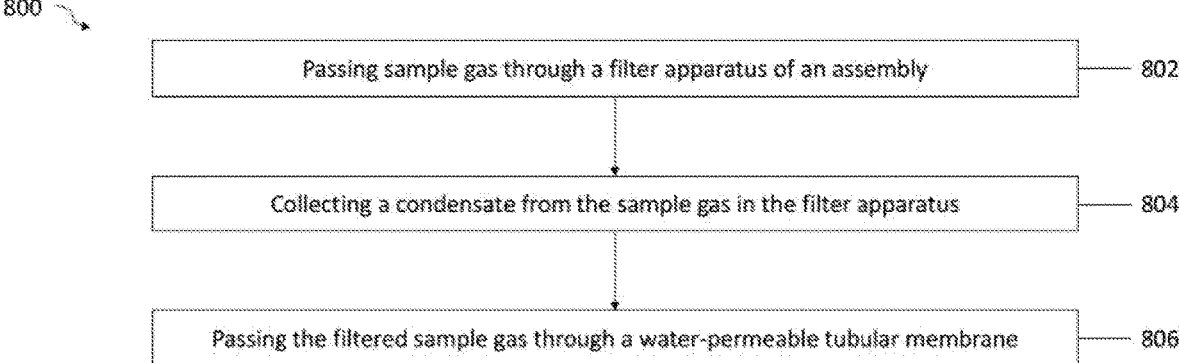
FIG. 8 is a flowchart of an example method.

Further provided herein is a method for maintaining a condensate pH from an assembly for humidity conditioning and filtering a sample gas in a therapeutic gas delivery device. A flowchart as seen in FIG. 8 is presented in accordance with an example embodiment. The method is provided by way of example, as there are a variety of ways to carry out the method. The method 800 described below can be carried out using the configurations illustrated in the figures, for example, and various elements of those figures are referenced in explaining example method 800. Each block represents one or more processes, methods, or subroutines, carried out in the example method 800. Furthermore, the illustrated order of blocks of FIG. 8 is illustrative only and the order of the blocks can change according to the present disclosure. Additional blocks may be added or fewer blocks may be utilized, without departing from this disclosure.

The example method 800 is a method for maintaining a condensate pH from an assembly for humidity conditioning and filtering a sample gas in a therapeutic gas delivery device. The example method can begin at block 802. At block 802, the method includes passing the sample gas through a filter apparatus (e.g., sample gas filter) of an assembly. The sample gas can be provided to the filter apparatus at a sample gas inlet. The sample gas can flow through the sample gas inlet to a first filter membrane. The first filter membrane may be hydrophobic and/or oleophobic. At the first filter membrane, liquids (e.g., humidity, water vapor, moisture from humidified air, other liquids in a vapor state, nebulized liquids, nebulized medical solutions and suspensions, etc.) may be filtered out of the sample gas. The first filter membrane can also filter saline solution from the sample gas. The sample gas may then pass through a second filter membrane. At the second filter membrane, liquids (humidity, water vapor, moisture from humidified air, other liquids in a vapor state, nebulized liquids, nebulized medical solutions and suspensions, etc.) may be filtered out of the sample gas.

At block 804, the method includes collecting a condensate from the sample gas in the filter apparatus. The liquids filtered by the first filter membrane can be collected in a first reservoir located in a first chamber of the filter apparatus. The first reservoir can also collect the saline solution filtered by the first filter membrane. The liquids filtered by the second filter membrane may be collected in a second reservoir located in a second chamber of the sample gas filter. A condensate pH level of 5.0 to 6.0 may be maintained in the condensate collected. Maintaining the condensate at a pH level of 5.0 to 6.0 ensures that any salt or sodium from the saline solution is filtered before entering the water-permeable tubular membrane, preventing any reactions in the water-permeable tubular membrane that may produce hydrochloric acid.

At block 806, the method includes passing the filtered sample gas through a water-permeable tubular membrane of the assembly. The sample gas leaving the water-permeable tubular membrane is a humidity conditioned gas. The water-permeable tubular membrane can be contained in a venti-lated cap connected to the sample gas filter. The ventilated cap can have at least one ventilation aperture to allow ambient air to contact the water-permeable tubular mem-brane. When the ambient air contacts the outer surfaces of the water-permeable tubular membrane, the water-perme-able tubular membrane can release water vapor from the sample gas to humidity condition the sample gas. The sample gas is humidity conditioned to have the same humid-ity as the ambient air by the water-permeable tubular mem-brane.

The sample gas can be humidity conditioned at a confi-dence level of at least 98%, 99%, 99.5%, 99.9%, or 99.95%. The humidity conditioned gas can be substantially free of saline. The humidity conditioned gas can be 98%, 99%, 99.5%, or 99.95% free of saline.

By filtering the liquids, including saline solution, before allowing the liquids to reach the water-permeable tubular membrane, the production of hydrochloric acid is prevented or reduced. Preventing or reducing the production of hydro-chloric acid can greatly reduce corrosion of the filter appa-ratus and corrosion of the therapeutic gas delivery device. Additionally, by preventing sodium from reacting with the water-permeable tubular membrane, blockage of the sample line, sample pump, and/or water-permeable tubular mem-brane can be greatly reduced. A blockage of the sample line connected to the assembly, a blockage of a pump connected to the sample line, corrosion of the sample gas filter, and/or corrosion in the therapeutic gas delivery device can be reduced or prevented at a confidence level of 98%.

The method can include maintaining the condensate at a pH of about 5.0 to about 6.0. In another example, the assembly can maintain the condensate at a pH of about 5.3 to about 6.0. In a further example, the assembly can maintain the condensate at a pH of about 5.4 to about 5.6.

Figure 9:
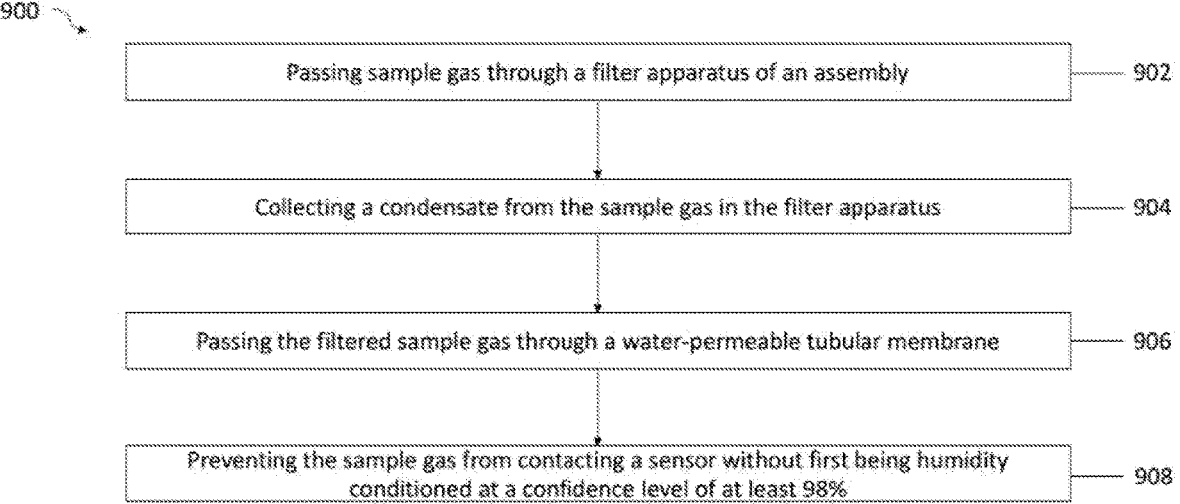
FIG. 9 is a flowchart of an example method.

Further provided herein is a method for preventing deg-radation or corrosion in a therapeutic gas delivery device. A flowchart as seen in FIG. 9 is presented in accordance with an example embodiment. The method is provided by way of example, as there are a variety of ways to carry out the method. The method 900 described below can be carried out using the configurations illustrated in the figures, for example, and various elements of those figures are refer-enced in explaining example method 900. Each block rep-resents one or more processes, methods, or subroutines, carried out in the example method 900. Furthermore, the illustrated order of blocks of FIG. 9 is illustrative only and the order of the blocks can change according to the present disclosure. Additional blocks may be added or fewer blocks may be utilized, without departing from this disclosure.

The example method 900 is a method for preventing degradation or corrosion in a therapeutic gas delivery device. The example method can begin at block 902. At block 902, the method includes passing the sample gas through a filter apparatus (e.g., sample gas filter) of an assembly. The sample gas can be provided to the filter apparatus at a sample gas inlet. The sample gas can flow through the sample gas inlet to a first filter membrane. The first filter membrane may be hydrophobic and/or oleopho-bic. At the first filter membrane, liquids (e.g., humidity, water vapor, moisture from humidified air, other liquids in a vapor state, nebulized liquids, nebulized medical solutions and suspensions, etc.) may be filtered out of the sample gas. The first filter membrane can also filter saline solution from the sample gas. The sample gas may then pass through a second filter membrane. At the second filter membrane, liquids (humidity, water vapor, moisture from humidified air, other liquids in a vapor state, nebulized liquids, nebulized medical solutions and suspensions, etc.) may be filtered out of the sample gas.

At block 904, the method includes collecting a condensate from the sample gas in the filter apparatus. The liquids filtered by the first filter membrane can be collected in a first reservoir located in a first chamber of the filter apparatus. The first reservoir can also collect the saline solution blocked by the first filter membrane. The liquids filtered by the second filter membrane may be collected in a second reservoir located in a second chamber of the sample gas filter. A condensate pH level of 5.0 to 6.0 may be maintained in the condensate collected. Maintaining the condensate at a pH level of 5.0 to 6.0 ensures that any salt or sodium from the saline solution is filtered before entering the water-permeable tubular membrane, preventing any reactions in the water-permeable tubular membrane that may produce hydrochloric acid.

At block 906, the method includes passing the filtered sample gas through a water-permeable tubular membrane of the assembly. The sample gas leaving the water-permeable tubular membrane is a humidity conditioned gas. The water-permeable tubular membrane can be contained in a venti-lated cap connected to the sample gas filter. The ventilated cap can have at least one ventilation aperture to allow ambient air to contact the water-permeable tubular mem-brane. When the ambient air contacts the outer surfaces of the water-permeable tubular membrane, the water-perme-able tubular membrane can release water vapor from the sample gas to humidity condition the sample gas. The sample gas is humidity conditioned to have the same humid-ity as the ambient air by the water-permeable tubular mem-brane.

The humidity conditioned gas can be substantially free of saline. The humidity conditioned gas can be 98%, 99%, 99.5%, or 99.95% free of saline.

By filtering the liquids, including saline solution, before allowing the liquids to reach the water-permeable tubular membrane, the production of hydrochloric acid is prevented or reduced. Preventing or reducing the production of hydro-chloric acid can greatly reduce corrosion of the sample gas filter and corrosion of the therapeutic gas delivery device. Additionally, by preventing sodium from reacting with the water-permeable tubular membrane, blockage of the sample line, sample pump, and/or water-permeable tubular mem-brane can be greatly reduced. A blockage of the sample line connected to the assembly, a blockage of a pump connected to the sample line, corrosion of the sample gas filter, and/or corrosion in the therapeutic gas delivery device can be reduced or prevented at a confidence level of 98%.

The method can include maintaining the condensate at a pH of about 5.0 to about 6.0. In another example, the assembly can maintain the condensate at a pH of about 5.3 to about 6.0. In a further example, the assembly can maintain the condensate at a pH of about 5.4 to about 5.6.

At block 908, the method includes preventing the sample gas from contacting a sensor without first being humidity conditioned at a confidence level of 98%. The sample gas may be humidity conditioned by the water-permeable tubular membrane The sample gas can be humidity conditioned at a confidence level of 98%, 98.5%, 99%, 99.5%, 99.95%, or 99.99%.

Figure 10:
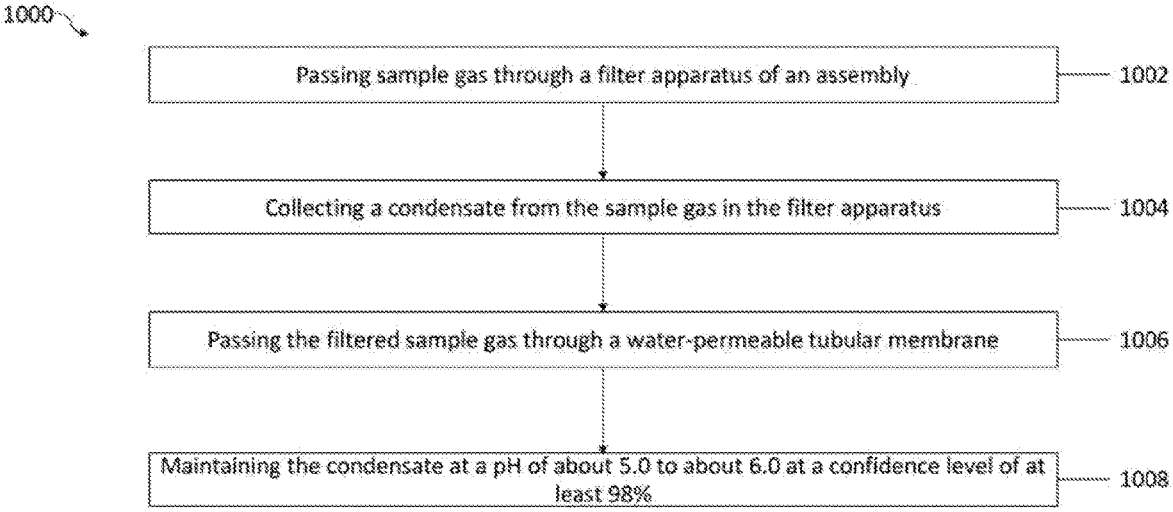
FIG. 10 is a flowchart of an example method.

Further provided herein is a method for preventing degradation or corrosion in a therapeutic gas delivery device. A flowchart as seen in FIG. 10 is presented in accordance with an example embodiment. The method is provided by way of example, as there are a variety of ways to carry out the method. The method 1000 described below can be carried out using the configurations illustrated in the figures, for example, and various elements of those figures are referenced in explaining example method 1000. Each block represents one or more processes, methods, or subroutines, carried out in the example method 1000. Furthermore, the illustrated order of blocks of FIG. 10 is illustrative only and the order of the blocks can change according to the present disclosure. Additional blocks may be added or fewer blocks may be utilized, without departing from this disclosure.

The example method 1000 is a method for preventing degradation or corrosion in a therapeutic gas delivery device. The example method can begin at block 1002. At block 1002, the method includes passing the sample gas through a filter apparatus (e.g., sample gas filter) of an assembly. The sample gas can be provided to the filter apparatus at a sample gas inlet. The sample gas can flow through the sample gas inlet to a first filter membrane. The first filter membrane may be hydrophobic and/or oleophobic. At the first filter membrane, liquids (e.g., humidity, water vapor, moisture from humidified air, other liquids in a vapor state, nebulized liquids, nebulized medical solutions and suspensions, etc.) may be filtered out of the sample gas. The first filter membrane can also filter saline solution from the sample gas. The sample gas may then pass through a second filter membrane. At the second filter membrane, liquids (humidity, water vapor, moisture from humidified air, other liquids in a vapor state, nebulized liquids, nebulized medical solutions and suspensions, etc.) may be filtered out of the sample gas.

At block 1004, the method includes collecting a condensate from the sample gas in the filter apparatus. The liquids filtered by the first filter membrane can be collected in a first reservoir located in a first chamber of the filter apparatus. The first reservoir can also collect the saline solution blocked by the first filter membrane. The liquids filtered by the second filter membrane may be collected in a second reservoir located in a second chamber of the sample gas filter.

At block 1006, the method includes passing the filtered sample gas through a water-permeable tubular membrane of the assembly. The sample gas leaving the water-permeable tubular membrane is a humidity conditioned gas. The water-permeable tubular membrane can be contained in a ventilated cap connected to the sample gas filter. The ventilated cap can have at least one ventilation aperture to allow ambient air to contact the water-permeable tubular membrane. When the ambient air contacts the outer surfaces of the water-permeable tubular membrane, the water-permeable tubular membrane can release water vapor from the sample gas to humidity condition the sample gas. The sample gas is humidity conditioned to have the same humidity as the ambient air by the water-permeable tubular membrane.

The sample gas can be humidity conditioned at a confidence level of at least 98%, 99%, 99.5%, 99.9%, or 99.95%. The humidity conditioned gas can be substantially free of saline. The humidity conditioned gas can be 98%, 99%, 99.5%, or 99.95% free of saline.

At block 1008, the method includes maintaining the condensate at a pH of about 5.0 to about 6.0 at a confidence level of 98%. Maintaining the condensate at a pH level of 5.0 to 6.0 ensures that any salt or sodium from the saline solution is filtered before entering the water-permeable tubular membrane, preventing any reactions in the water-permeable tubular membrane that may produce hydrochloric acid.

In another example, the assembly can maintain the condensate at a pH of about 5.3 to about 6.0. In a further example, the assembly can maintain the condensate at a pH of about 5.4 to about 5.6.

By filtering the liquids, including saline solution, before allowing the liquids to reach the water-permeable tubular membrane, the production of hydrochloric acid is prevented or reduced. Preventing or reducing the production of hydrochloric acid can greatly reduce corrosion of the sample gas filter and corrosion of the therapeutic gas delivery device. Additionally, by preventing sodium from reacting with the water-permeable tubular membrane blockage of the sample line, sample pump, and/or water-permeable tubular membrane can be greatly reduced. A blockage of the sample line connected to the assembly, a blockage of a pump connected to the sample line, corrosion of the sample gas filter, and/or corrosion in the therapeutic gas delivery device can be reduced or prevented at a confidence level of 98%.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

Reference an "embodiment", "aspect," "instance," or "example" means that a particular feature, structure, or characteristic described in connection with the embodiment is included in at least one embodiment of the disclosure. The appearances of the phrase in one "embodiment", "aspect," "instance," or "example" in various places in the specification are not necessarily all referring to the same embodiment, nor are separate or alternative embodiments mutually exclusive of other embodiments. Moreover, various features are described which may be exhibited by some embodiments and not by others.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term. Likewise, the disclosure is not limited to various embodiments given in this specification.

EXAMPLES

Results of operating the therapeutic gas delivery device with different configurations of the sample gas filter assembly are shown in Table 1. Devices 6 and 10 are sample gas filter assemblies using the configuration described in the disclosure above. Devices 6 and 10 consisted of a sample gas line providing sample gas to a sample gas inlet and a filter apparatus comprising two filter membranes. The sample gas filter collected a condensate and the pH of the condensate was measured. The sample gas was then provided to a water-permeable tubular membrane via the sample gas outlet and water-permeable tubular membrane inlet conduit. The sample gas flowed through the water-permeable tubular membrane and discharged at the assembly outlet. The sample gas then entered the gas sensor module of the therapeutic gas delivery device. Device 9 consisted of another configuration of the sample gas filter assembly. The gas first flowed through the water-permeable tubular membrane first, then through the filter apparatus, and then to the therapeutic gas delivery device through the sample gas outlet. The condensate was collected in the sample gas filter and the pH of the condensate was measured. As shown in Table 1, by filtering the sample gas before humidity conditioning it in the water-permeable tubular membrane, corrosive acid production (pH of 1-2) is reduced or prevented.

TABLE 1

| Condensate pH Results | | | |
| --- | --- | --- | --- |
| Device | Configuration | Time | Condensate pH |
| 6 | 2-stage, revised | Oct. 12, 2018 11:26 | 6-7 |
| 9 | 2-stage, standard | Oct. 12, 2018 13:03 | 1 |
| 9 | 2-stage, standard | Oct. 12, 2018 17:27 | 1-2 |
| 10 | 2-stage, revised | Oct. 12, 2018 11:15 | 6-7 |
| 10 | 2-stage, revised | Oct. 12, 2018 11:15 | 6-7 |

Exemplary Embodiments

The following is a list of exemplary embodiments, and may include combinations thereof.

Embodiment 1: A filter assembly for a therapeutic gas delivery device, the assembly comprising: a filter apparatus comprising an inlet, an outlet, and at least one reservoir and at least one filter membrane between the inlet and the outlet, wherein the filter apparatus is operable to remove water vapor from a sample gas and collect a condensate in the at least one reservoir; a water-permeable tubular membrane fluidly connected to the outlet of the filter apparatus, and a ventilated cap connected to the filter apparatus and surrounding the outlet, the ventilated cap comprising a ventilation aperture.

Embodiment 2: The assembly of embodiment 1, wherein the water-permeable tubular membrane is configured to humidity condition the sample gas.

Embodiment 3: The assembly of embodiment 1, wherein the ventilated cap comprises a plurality of ventilation apertures.

Embodiment 4: The assembly of embodiment 1, wherein the ventilated cap is configured to contain and secure the water-permeable tubular membrane.

Embodiment 5: The assembly of embodiment 1, wherein the water-permeable tubular membrane is formed of a sulfonated tetrafluoroethylene based fluoropolymer-copolymer.

Embodiment 6: The assembly of embodiment 1, wherein the water-permeable tubular membrane is tubing comprising a sulfonated tetrafluoroethylene based fluoropolymer-copolymer.

Embodiment 7: The assembly of embodiment 1, wherein the filter apparatus comprises: a housing having a sample gas inlet and a sample gas outlet, the sample gas inlet operable to receive a sample gas from a sample line connected to an inspiratory line of the therapeutic gas delivery device; a first filter membrane; and a first reservoir disposed between the sample gas inlet and the first filter membrane; and a second chamber disposed in the housing, the second chamber comprising: a second filter membrane; and a second reservoir disposed between the first filter membrane and the sample gas outlet.

Embodiment 8: The assembly of embodiment 7, wherein the first reservoir and the second reservoir are oriented axially such that the filter apparatus is operable to be used in any axial orientation.

Embodiment 9: The assembly of embodiment 7, wherein the housing, each of the chambers, and each of the filter membranes have a substantially circular cross-section.

Embodiment 10: The assembly of embodiment 1, wherein the at least one reservoir is large enough to accommodate water for 12 hours of continuous use.

Embodiment 11: The assembly of embodiment 1, wherein the at least one reservoir has a volume of at least 10 cubic centimeters.

Embodiment 12: The assembly of embodiment 1, wherein the assembly is configured to be installed in the therapeutic gas delivery device with one hand.

Embodiment 13: A method for humidity conditioning and filtering a sample gas in a therapeutic gas delivery device, the method comprising: passing the sample gas through a filter apparatus of an assembly; collecting a condensate from the sample gas in the filter apparatus; and passing the filtered sample gas through a water-permeable tubular membrane of the assembly, wherein the sample gas leaving the water-permeable tubular membrane is a humidity conditioned sample gas.

Embodiment 14: The method of embodiment 13, wherein the sample gas leaving the water-permeable tubular membrane is a humidity conditioned sample gas at a confidence level of at least 98%.

Embodiment 15: The method of embodiment 13, wherein the sample gas leaving the water-permeable tubular membrane is a humidity conditioned sample gas at a confidence level of at least 99%.

Embodiment 16: The method of embodiment 13, wherein the sample gas leaving the water-permeable tubular membrane is a humidity conditioned sample gas at a confidence level of at least 99.5%.

Embodiment 17: The method of embodiment 13, wherein the sample gas leaving the water-permeable tubular membrane is a humidity conditioned sample gas at a confidence level of at least 99.9%.

Embodiment 18: The method of embodiment 13, wherein the sample gas leaving the water-permeable tubular membrane is a humidity conditioned sample gas at a confidence level of at least 99.95%.

Embodiment 19: The method of embodiment 13, further comprising exposing outer surfaces of the water-permeable tubular membrane to an ambient air flow.

Embodiment 20: The method of embodiment 13, wherein the humidity conditioned sample gas is substantially free of saline.

Embodiment 21: The method of embodiment 13, further comprising reducing or preventing production of HCl within the therapeutic gas delivery device.

Embodiment 22: The method of embodiment 13, further comprising reducing or preventing a blockage of a sample line connected to the assembly, a blockage of a pump connected to the sample line, corrosion of the filter apparatus, and/or corrosion in the therapeutic gas delivery device at a confidence level of at least 98%.

Embodiment 23: The method of embodiment 13, wherein the assembly maintains the condensate at a pH of about 5.0 to about 6.0.

Embodiment 24: The method of embodiment 13, wherein the assembly maintains the condensate of about pH 5.3 to about 6.0.

Embodiment 25: The method of embodiment 13, wherein the assembly maintains the condensate of about pH 5.4 to about 5.6.

Embodiment 26: A method of maintaining a condensate pH from an assembly for humidity conditioning and filtering a sample gas in a therapeutic gas delivery device, the method comprising: passing the sample gas through a filter apparatus of the assembly; collecting a condensate from the sample gas in the filter apparatus; and passing the filtered sample gas through a water-permeable tubular membrane of the assembly, wherein the sample gas leaving the water-permeable tubular membrane is a humidity conditioned sample gas, wherein the assembly maintains the condensate at pH 5.0-6.0.

Embodiment 27: The method of embodiment 26, wherein the humidity conditioned sample gas is substantially free of saline.

Embodiment 28: The method of embodiment 26, further comprising exposing outer surfaces of the water-permeable tubular membrane to an ambient air flow.

Embodiment 29: The method of embodiment 26, wherein the assembly reduces or prevents production of HCl within the therapeutic gas delivery device.

Embodiment 30: The method of embodiment 26, wherein the assembly reduces or prevents a blockage of a sample line connected to the assembly, a blockage of a pump connected to the sample line, corrosion of the filter apparatus, or corrosion in the therapeutic gas delivery device.

Embodiment 31: A method for preventing degradation or corrosion in a therapeutic gas delivery device, the method comprising: passing a sample gas through a filter apparatus of an assembly; collecting a condensate from the sample gas in the filter apparatus; passing the filtered sample gas through a water-permeable tubular membrane of the assembly, wherein the sample gas leaving the water-permeable tubular membrane is a humidity conditioned sample gas, and preventing the sample gas from contacting a sensor without first being humidity conditioned at a confidence level of at least 98%.

Embodiment 32: A method for preventing degradation or corrosion in a therapeutic gas delivery device, the method comprising: passing a sample gas through a filter apparatus of an assembly; collecting a condensate from the sample gas in the filter apparatus; passing the filtered sample gas through a water-permeable tubular membrane of the assembly, wherein the sample gas leaving the water-permeable tubular membrane is a humidity conditioned sample gas, and maintaining the condensate at a pH of about 5.0 to about 6 at a confidence level of at least 98%.

Having described several embodiments, it will be recognized by those skilled in the art that various modifications, alternative constructions, and equivalents may be used without departing from the spirit of the invention. Additionally, a number of well-known processes and elements have not been described in order to avoid unnecessarily obscuring the present invention. Accordingly, the above description should not be taken as limiting the scope of the invention.

Those skilled in the art will appreciate that the presently disclosed embodiments teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present systems and methods, which, as a matter of language, might be said to fall therebetween.

What is claimed is:

1. A filter assembly for a therapeutic gas delivery device, the assembly comprising:
a filter apparatus comprising an inlet, an outlet, and at least one reservoir and at least one filter membrane between the inlet and the outlet, wherein the filter apparatus is operable to remove water vapor from a sample gas and collect a condensate in the at least one reservoir;
a water-permeable tubular membrane fluidly connected to the outlet of the filter apparatus, and
a ventilated cap connected to the filter apparatus and surrounding the outlet, the ventilated cap comprising a ventilation aperture.

2. The assembly of claim 1, wherein the water-permeable tubular membrane is configured to humidity condition the sample gas.

3. The assembly of claim 1, wherein the ventilated cap comprises a plurality of ventilation apertures.

4. The assembly of claim 1, wherein the ventilated cap is configured to contain and secure the water-permeable tubular membrane.

5. The assembly of claim 1, wherein the water-permeable tubular membrane is formed of a sulfonated tetrafluoroethylene based fluoropolymer-copolymer.

6. The assembly of claim 1, wherein the water-permeable tubular membrane is tubing comprising a sulfonated tetrafluoroethylene based fluoropolymer-copolymer.

7. The assembly of claim 1, wherein the filter apparatus comprises:
a housing inlet operable to receive a sample gas from a sample line connected to an inspiratory line of the therapeutic gas delivery device;
a first chamber disposed in the housing, the first chamber comprising:
a first filter membrane; and
a first reservoir disposed between the inlet and the first filter membrane; and
a second chamber disposed in the housing, the second chamber comprising:
a second filter membrane; and
a second reservoir disposed between the first filter membrane and the outlet.

8. The assembly of claim 7, wherein the first reservoir and the second reservoir are oriented axially such that the filter apparatus is operable to be used in any axial orientation.

9. The assembly of claim 7, wherein the housing, each of the chambers, and each of the filter membranes have a substantially circular cross-section.

10. The assembly of claim 1, wherein the at least one reservoir is large enough to accommodate water for 12 hours of continuous use.

11. The assembly of claim 1, wherein the at least one reservoir has a volume of at least 10 cubic centimeters.

12. The assembly of claim 1, wherein the assembly is configured to be installed in the therapeutic gas delivery device with one hand.

13. A method for humidity conditioning and filtering a sample gas in a therapeutic gas delivery device, the method comprising:

passing the sample gas through a filter apparatus of an assembly;

collecting a condensate from the sample gas in the filter apparatus; and passing a filtered sample gas through a water-permeable tubular membrane of the assembly, wherein the sample gas leaving the water-permeable tubular membrane is a humidity conditioned sample gas.

14. The method of claim 13, wherein the sample gas leaving the water-permeable tubular membrane is a humidity conditioned sample gas.

15. The method of claim 13, further comprising exposing outer surfaces of the water-permeable tubular membrane to an ambient air flow.

16. The method of claim 13, wherein the humidity conditioned sample gas is substantially free of saline.

17. The method of claim 13, further comprising reducing or preventing production of HCl within the therapeutic gas delivery device.

18. The method of claim 13, further comprising reducing or preventing a blockage of a sample line connected to the assembly, a blockage of a pump connected to the sample line, corrosion of the filter apparatus, and/or corrosion in the therapeutic gas delivery device.

19. The method of claim 13, wherein the assembly maintains the condensate at a pH of about 5.0 to about 6.0.

20. A method for preventing degradation or corrosion in a therapeutic gas delivery device, the method comprising:

passing a sample gas through a filter apparatus of an assembly;

collecting a condensate from the sample gas in the filter apparatus;

passing a filtered sample gas through a water-permeable tubular membrane of the assembly, wherein the sample gas leaving the water-permeable tubular membrane is a humidity conditioned sample gas, and preventing the sample gas from contacting a sensor without first being humidity conditioned and/or maintaining the condensate at a pH of about 5.0 to about 6.0.

* * * * *